US012410469B2

(12) United States Patent
Ranik et al.

(10) Patent No.: US 12,410,469 B2
(45) Date of Patent: Sep. 9, 2025

(54) METHODS AND COMPOSITIONS FOR SEQUENCING LIBRARY NORMALIZATION

(71) Applicant: Watchmaker Genomics, Inc., Boulder, CO (US)

(72) Inventors: Martin Ranik, Boulder, CO (US); Eric van der Walt, Cape Town (ZA); Clara Ross, Lafayette, CO (US); Craig Marshall, Boulder, CO (US); Lindsay Peterkin, Longmont, CO (US); Brian Kudlow, Boulder, CO (US); Travis J. Sanders, Boulder, CO (US)

(73) Assignee: Watchmaker Genomics, Inc., Boulder, CO (US)

( * ) Notice: Subject to any disclaimer, the term of this patent is extended or adjusted under 35 U.S.C. 154(b) by 0 days.

(21) Appl. No.: 18/492,763

(22) Filed: Oct. 23, 2023

(65) Prior Publication Data

US 2024/0132942 A1   Apr. 25, 2024
US 2024/0229115 A9   Jul. 11, 2024

Related U.S. Application Data

(63) Continuation of application No. PCT/US2023/077435, filed on Oct. 20, 2023.

(60) Provisional application No. 63/516,033, filed on Jul. 27, 2023, provisional application No. 63/380,488, filed on Oct. 21, 2022.

(51) Int. Cl.
  *C12Q 1/6834* (2018.01)
  *C12N 9/22* (2006.01)

(52) U.S. Cl.
  CPC .......... *C12Q 1/6834* (2013.01); *C12N 9/22* (2013.01); *C12N 2310/20* (2017.05); *C12Q 2600/166* (2013.01)

(58) Field of Classification Search
  CPC .. C12Q 1/6834; C12Q 2600/166; C12N 9/22; C12N 2310/20
  See application file for complete search history.

(56) References Cited

U.S. PATENT DOCUMENTS

| | | | |
|---|---|---|---|
| 10,081,829 B1 | 9/2018 | Shuber et al. | |
| 10,113,167 B2 | 10/2018 | Doudna et al. | |
| 10,358,658 B2 | 7/2019 | Doudna et al. | |
| 10,370,700 B2 | 8/2019 | Shuber et al. | |
| 10,415,061 B2 | 9/2019 | Doudna et al. | |
| 10,457,969 B2 | 10/2019 | Cann et al. | |
| 10,487,341 B2 | 11/2019 | Doudna et al. | |
| 10,513,712 B2 | 12/2019 | Doudna et al. | |
| 10,527,608 B2 | 1/2020 | Shuber et al. | |
| 10,577,649 B2 | 3/2020 | Mandell | |
| 10,676,726 B2 * | 6/2020 | Gersbach | C12N 9/22 |
| 10,774,365 B2 | 9/2020 | Carpenter et al. | |
| 10,844,378 B2 | 11/2020 | Siksnys et al. | |
| 11,008,590 B2 | 5/2021 | Doudna et al. | |
| 11,085,078 B2 * | 8/2021 | Heron | C12Q 1/6869 |
| 2015/0232929 A1 * | 8/2015 | Stephens | C12Q 1/6858 506/4 |
| 2018/0171360 A1 | 6/2018 | Cameron et al. | |
| 2018/0355380 A1 | 12/2018 | Shuber et al. | |
| 2018/0355406 A1 | 12/2018 | Glover | |
| 2018/0355408 A1 | 12/2018 | Shuber | |
| 2018/0355409 A1 | 12/2018 | Shuber | |
| 2018/0355417 A1 | 12/2018 | Shuber et al. | |
| 2018/0355419 A1 | 12/2018 | Glover | |
| 2018/0355436 A1 | 12/2018 | Shuber et al. | |
| 2018/0355437 A1 | 12/2018 | Shuber | |
| 2019/0002964 A1 | 1/2019 | Shuber | |
| 2019/0032116 A1 | 1/2019 | Shuber | |
| 2019/0071716 A1 | 3/2019 | Shuber | |
| 2019/0085318 A1 | 3/2019 | Shuber | |
| 2019/0345539 A1 | 11/2019 | Shuber et al. | |
| 2019/0390254 A1 * | 12/2019 | Osborne | C12Q 1/6806 |
| 2020/0216877 A1 | 7/2020 | Betts et al. | |
| 2021/0040537 A1 | 2/2021 | Shuber | |
| 2021/0155972 A1 | 5/2021 | Shuber | |
| 2023/0122979 A1 | 4/2023 | Brown | |

FOREIGN PATENT DOCUMENTS

| | | | |
|---|---|---|---|
| EP | 3172321 A1 | 5/2017 | |
| WO | WO 2007/048629 A2 | 5/2007 | |
| WO | WO 2018/048957 A2 | 3/2018 | |

(Continued)

OTHER PUBLICATIONS

Doudna "Molecular Mechanisms of RNA Interference" Annu. Rev. Biophys (2013) 42:217-39. (Year: 2013).*
Invitation to Pay Additional Fees for Application No. PCT/US2023/077435, mailed Feb. 6, 2024.
Sashital, Prokaryotic Argonaute Uses an All-in-One Mechanism to Provide Host Defense. Mol Cell. Mar. 16, 2017;65(6):957-958. doi: 10.1016/j.molcel.2017.03.002.

(Continued)

*Primary Examiner* — Nancy J Leith
*Assistant Examiner* — Kelly Nichet Hassell
(74) *Attorney, Agent, or Firm* — Wolf, Greenfield & Sacks, P.C.

(57) ABSTRACT

Disclosed herein are methods and compositions for normalizing polynucleotide concentration. Normalizing may be accomplished using polynucleotide binding proteins (e.g., catalytically inactive CRISPR protein or catalytically inactive Argonaute proteins). The polynucleotide binding proteins may bind to the adapter sequences of a target polynucleotide. Thus, adding the same amount of a polynucleotide binding proteins to different samples and then extracting the polynucleotide protein is shown herein to extract similar amounts of target polynucleotides from the different samples.

25 Claims, 9 Drawing Sheets

Specification includes a Sequence Listing.

(56) References Cited

FOREIGN PATENT DOCUMENTS

| WO | WO-2018136881 A1 | * | 7/2018 | ......... | C12N 15/1068 |
|----|------------------|---|--------|-----------|--------------|
| WO | WO 2018/231945 A1 | | 12/2018 | | |
| WO | WO-2020131383 A1 | * | 6/2020 | ......... | C12N 15/1065 |
| WO | WO 2020/172362 A1 | | 8/2020 | | |

OTHER PUBLICATIONS

Wu et al., Argonaute proteins: Structural features, functions and emerging roles. J Adv Res. Apr. 29, 2020:24:317-324. doi: 10.1016/j.jare.2020.04.017. eCollection Jul. 2020.

Yin et al., Structure-guided chemical modification of guide RNA enables potent non-viral in vivo genome editing. Nat Biotechnol. Dec. 2017;35(12):1179-1187. doi: 10.1038/nbt.4005. Epub Nov. 13, 2017. With supplemental information.

International Search Report and Written Opinion for Application No. PCT/US2023/077435, mailed Apr. 10, 2024.

Van Der Valk et al., Estimating the rate of index hopping on the Illumina HiSeq X platform. bioRxiv. Mar. 27, 2018. doi: https://doi.org/10.1101/179028.

\* cited by examiner

METHODS AND COMPOSITIONS FOR SEQUENCING LIBRARY NORMALIZATION

RELATED APPLICATIONS

This application claims the benefit under 35 U.S.C. § 365(c) and § 120 and is a continuation of International Patent Application Number PCT/US2023/077435, filed Oct. 20, 2023, which claims the benefit of 35 U.S.C. § 119(e) to U.S. Provisional Application No. 63/380,488, filed Oct. 21, 2022, entitled "Methods for Sequencing Library Normalization", and to U.S. Provisional Application No. 63/516,033, filed Jul. 27, 2023, entitled "Methods and Compositions for Sequencing Library Normalization", the entire contents of each of which are incorporated herein by reference.

REFERENCE TO AN ELECTRONIC SEQUENCE LISTING

The content of the electronic sequence (W109470000US02-SUBSEQ-ARM.xml; Size: 54,128 bytes; and Date of Creation: Nov. 15, 2023) is herein incorporated by reference in its entirety.

BACKGROUND

Massively parallel, deep sequencing, or next generation sequencing (NGS) enables large-scale DNA and RNA sequencing. These methods involve parallel multiplexed analysis of nucleic acid sequences on a massive scale, allowing for millions to billions of sequences from individual strands to be analyzed separately but simultaneously.

The multiplexed analysis can be challenging because different samples to be analyzed often vary in the amount of nucleic acids present, which can lead to inaccuracies where low concentration samples are under-sequenced and high concentration samples are over-sequenced. Therefore, various methods for the normalization of nucleic acid concentrations between samples have been employed. Spectrophotometry, electrophoreses, fluorometry, and quantitative PCR (qPCR) have been used to detect the concentration of nucleic acids in a sample in order to normalize concentrations between samples. Each of these methods has disadvantages such as inaccuracy introduced by manual adjustments being made, lack of sensitivity, and multiple steps involving substantial time and/or expense.

SUMMARY

This disclosure describes, in some aspects, methods and compositions for normalizing polynucleotide concentrations between two or more polynucleotide sequencing libraries. Polynucleotide preparation for sequencing (e.g., next-generation sequencing (NGS)) often involves adding adapter polynucleotide sequences to the polynucleotides. Certain technologies, like ILLUMINA sequencing, use the adapter sequences to perform sequencing of the polynucleotides. It is recognized herein that these adapter sequences can be leveraged to normalize polynucleotide concentrations between different polynucleotide sequencing libraries. Specifically, it is recognized that polynucleotide sequencing library normalization may be achieved by contacting a polynucleotide sequencing library with a predetermined amount of a ribonucleoprotein that binds to an adapter sequence of the polynucleotide library (e.g., a catalytically inactive CRISPR associated protein (dCAS)-guide RNA (gRNA) complex) and extracting the polynucleotides that (1) comprise the adapter and (2) are bound by the ribonucleoprotein complex. It is demonstrated that performing this method for multiple different polynucleotide sequencing libraries normalizes the concentration of polynucleotides between the polynucleotide sequencing libraries.

Accordingly, the present disclosure provides, in some aspects, method for normalizing the concentration of target polynucleotides between at least two samples each comprising target polynucleotides, the method comprising, for each sample of the at least two samples:

(i) obtaining the sample, wherein the target polynucleotides of the sample comprise an adapter sequence;

(ii) producing a solution, the producing comprising combining (a) the sample, (b) a predetermined concentration of a guide polynucleotide comprising a targeting region that is complementary to the adapter sequence of the target polynucleotides of the sample; and (c) a predetermined concentration of a dCas or a dArgonaute comprising an affinity tag, wherein the predetermined concentration of the dCas or the dArgonaute is cognate to the guide polynucleotide;

(iii) contacting the solution with a solid phase comprising an affinity tag binding molecule that is capable of binding to the affinity tag;

(iv) separating the solution from the solid phase; and (v) extracting the target polynucleotides from the solid phase to normalize the concentration of target polynucleotides between the two or more samples. In some embodiments, the targeting region is complementary to a static region of an adapter sequence. In some embodiments, the guide polynucleotide comprises a CRISPR-associated protein (Cas) guide RNA (gRNA) polynucleotide or an Argonaute guide polynucleotide. In some embodiments, the static region is a static region of a next-generation sequencing adapter sequence. In some embodiments, the targeting region is complementary to an adapter sequence of any one of SEQ ID NOs: 27-36. In some embodiments, the targeting region is complementary to an adapter sequence of any one of SEQ ID NOs: 27-28. In some embodiments, the targeting region is complementary to an adapter sequence of any one of SEQ ID NOs: 29-30. In some embodiments, the targeting region is complementary to an adapter sequence of any one of SEQ ID NOs: 31-32. In some embodiments, the targeting region is complementary to an adapter sequence any one of SEQ ID NOs: 33-34. In some embodiments, the targeting region is complementary to an adapter sequence of SEQ ID NO: 35. In some embodiments, the targeting region is complementary to an adapter sequence of SEQ ID NO: 36.

In some embodiments, the Cas gRNA polynucleotide targeting region is a homology region. In some embodiments, the Cas gRNA polynucleotide comprises a homology region of any one of SEQ ID NOs: 1-26. In some embodiments, the Cas gRNA polynucleotide comprises a homology region of SEQ ID NO: 1.

In some embodiments, the Argonaute guide polynucleotide is an siRNA, miRNA, piRNA, shRNA or siDNA.

In some embodiments, the guide polynucleotide is a DNA polynucleotide. In some embodiments, the guide polynucleotide is a RNA polynucleotide. In some embodiments, the guide polynucleotide comprises a modified nucleic acid. In some embodiments, the modified nucleic acid comprises 2'F RNA, 2'OMe RNA, and/or a phosphorothioate bonds (PS).

In some embodiments, the guide polynucleotide is a Cas gRNA polynucleotide and the Cas gRNA polynucleotide does not comprise a modified nucleic acid in a position that interacts with a Cas protein cognate to the gRNA. In some embodiments, the dCas is a catalytically-inactive Cpf1, C2c1, C2c3, C2c2, CasX, or CasY protein. In some embodiments, the dCas protein comprises an amino acid sequence of SEQ ID NO: 37.

In some embodiments, the dArgonaute is a catalytically-inactive LrAgo, PfAgo, TtAgo, AaAgo, AfAgo, MjAgo, MpAgo, NgAgo, RsAgo, CpAgo, IbAgo, KmAgo, or SeAgo.

In some embodiments, the affinity tag binding molecule comprises Ni2+ and the affinity tag comprises a His Tag.

In some embodiments, the affinity tag binding molecule comprises biotin and the affinity tag comprises avidin. In some embodiments, the affinity tag binding molecule comprises an anti-myc antibody and the affinity tag comprises a myc tag. In some embodiments, the affinity tag and corresponding affinity tag binding molecule are selected from Table 1.

In some embodiments, the solid phase comprises magnetic beads. In some embodiments, separating the solution from the solid phase comprises immobilizing the solid phase and washing the solid phase. In some embodiments, extracting the target polynucleotides from the solid phase comprises combining the solid phase and protease. In some embodiments, extracting the target polynucleotides from the solid phase comprises combining the solid phase and proteinase K in a solution sufficient for proteinase K activity. In some embodiments, proteinase K digests the dCas or dArgonaute that is bound to the solid phase thereby extracting the target polynucleotides.

In some embodiments, steps (i)-(v) are performed in sequential order.

In some embodiments, normalizing comprises making the concentration of the of target polynucleotides between the at least two samples within 15% of one another after normalization.

In some aspects, the present disclosure provides a method for normalizing the concentration of target polynucleotides between at least two samples each comprising target polynucleotides, the method comprising, for each sample of the at least two samples:
  (i) obtaining the sample, wherein the target polynucleotides of the sample comprise an adapter sequence;
  (ii) producing a solution, the producing comprising combining (a) the sample, (b) a predetermined concentration of a guide polynucleotide comprising a targeting region that is complementary to the adapter sequence of the target polynucleotides of the sample, and (c) a predetermined concentration of a dCas or a dArgonaute comprising an affinity tag; and
  (iii) contacting the solution with a pre-determined amount of a catalytically active Cas or Argonaute protein to normalize the concentration of target polynucleotides between the two or more samples.

In some embodiments, the dCas is a catalytically-inactive Cpf1, C2c1, C2c3, C2c2, CasX, Cas9, or CasY protein. In some embodiments, the dCas protein comprises an amino acid sequence having at least 95% identity to SEQ ID NO: 37. In some embodiments, the dCas protein comprises an amino acid sequence of SEQ ID NO: 37.

In some embodiments, the dArgonaute is a catalytically-inactive LrAgo, PfAgo, TtAgo, AaAgo, AfAgo, MjAgo, MpAgo, NgAgo, RsAgo, CpAgo, IbAgo, KmAgo, or SeAgo.

In some embodiments, step (ii) comprises binding of dCas or dArgonaute to the adapter sequences of at least some of the target polynucleotides. In some embodiments, the catalytically active Cas9 or Argonaute digests target polynucleotides that are not bound by the dCas9 or the dArgonaute. In some embodiments, normalizing comprises making the concentration of the of target polynucleotides between the at least two samples within 15% of one another after normalization. In some embodiments, normalizing comprises making the concentration of the of target polynucleotides between the at least two samples within 10% of one another after normalization. In some embodiments, the target polynucleotides comprise a first adapter sequence and a second adapter sequence, and wherein the guide polynucleotide targeting region is complementary to the first adapter sequence.

In some embodiments, the method further comprises, after step (i) and before step (ii):
  (a) contacting the sample with a primer encoding a nucleic acid sequence that is complementary to a portion of the second adapter sequence, wherein the portion of the adapter sequence is located in the proximal portion of the adapter sequence; and
  (b) contacting the sample with a DNA polymerase in conditions sufficient to promote primer extension.

In some embodiments, the portion of the adapter sequence comprises a nucleic acid sequence of any one of SEQ ID NOs: 28, 30, 32, and 34.

In some embodiments, the second adapter sequence is a 3' adapter sequence. In some embodiments, the second adapter sequence is a 5' adapter sequence.

In some aspects, the disclosure provides a guide polynucleotide comprising a targeting region that is complementary to an adapter sequence of any one of SEQ ID NOs: 28 and 30, 32, 34-36. In some embodiments, the guide polynucleotide comprises a CRISPR-associated protein (Cas) guide RNA (gRNA) polynucleotide or an Argonaute guide polynucleotide.

In some embodiments, the static region is a static region of a next-generation sequencing adapter sequence. In some embodiments, the targeting region is complementary to an adapter sequence of SEQ ID NO: 28. In some embodiments, the targeting region is complementary to an adapter sequence of SEQ ID NO: 30. In some embodiments, the targeting region is complementary to an adapter sequence of SEQ ID NO: 32. In some embodiments, the targeting region is complementary to an adapter sequence of SEQ ID NO: 34. In some embodiments, the targeting region is complementary to an adapter sequence of SEQ ID NO: 35. In some embodiments, the targeting region is complementary to an adapter sequence of any one of SEQ ID NOs: 36.

In some embodiments, the Cas gRNA polynucleotide targeting region is a homology region. In some embodiments, the Cas gRNA polynucleotide comprises a homology region of any one of SEQ ID NOs: 1-26. In some embodiments, the Cas gRNA polynucleotide comprises a homology region of SEQ ID NO: 1.

In some embodiments, the Argonaute guide polynucleotide is an siRNA, miRNA, piRNA, shRNA or siDNA.

In some embodiments, the guide polynucleotide is a DNA polynucleotide. In some embodiments, the guide polynucleotide is a RNA polynucleotide. In some embodiments, the guide polynucleotide comprises a modified nucleic acid. In some embodiments, the modified nucleic acid comprises 2'F RNA, 2'Ome RNA, and/or a phosphorothioate bonds (PS). In some embodiments, the guide polynucleotide is a Cas gRNA polynucleotide and the Cas gRNA polynucleotide does not comprise a modified nucleic acid in a position that interacts with a Cas protein cognate to the gRNA.

In some embodiments, the present disclosure provides herein a kit comprising (a) a guide polynucleotide described herein, and (b) a Cas protein or an Argonaute protein, or a polynucleotide sequence encoding a Cas protein or an Argonaute protein. In some embodiments, the Cas protein is a catalytically-inactive Cas protein (dCas). In some embodiments, the Cas protein is a Cas9 protein that is catalytically-inactive (dCas9). In some embodiments, the Cas9 protein comprises a D10A mutation and a H840A mutation. In some embodiments, the Cas protein is a catalytically-inactive Cpf1, C2c1, C2c3, C2c2, CasX, or CasY protein. In some embodiments, the dCas protein comprises an amino acid sequence having at least 95% identity to SEQ ID NO: 37. In some embodiments, the dCas protein comprises an amino acid sequence of SEQ ID NO: 37.

In some embodiments, the Argonaute protein is catalytically-inactive (dArgonaute). In some embodiments, the Argonaute protein is a CbAgo protein that is catalytically-inactive. In some embodiments, the Argonaute protein is a LrAgo, PfAgo, TtAgo, AaAgo, AfAgo, MjAgo, MpAgo, NgAgo, RsAgo, CpAgo, IbAgo, KmAgo, or SeAgo protein that is catalytically-inactive.

In some embodiments, the dArgonaute protein comprises an amino acid sequence having at least 95% identity to any one of SEQ ID NOs: 39-45. In some embodiments, the dArgonaute protein comprises an amino acid sequence of any one of SEQ ID NOs: 39-45.

In some embodiments, the kit further comprises a catalytically active Cas protein or a catalytically active Argonaute protein. In some embodiments, the catalytically active Cas protein comprises Cpf1, C2c1, C2c3, C2c2, CasX, Cas9, or CasY. In some embodiments, the catalytically active Argonaute protein comprises LrAgo, PfAgo, TtAgo, AaAgo, AfAgo, MjAgo, MpAgo, NgAgo, RsAgo, CpAgo, IbAgo, KmAgo, or SeAgo. In some embodiments, the guide polynucleotide is capable of binding to the Cas protein or the Argonaute protein to form a ribonucleoprotein complex and the ribonucleoprotein complex is capable of binding to an adapter sequence.

In some embodiments, the kit further comprises a primer that is complementary to a portion of an adapter sequence. In some embodiments, the portion of the adapter sequence is located in the proximal portion of the adapter sequence. In some embodiments, the portion of the adapter sequence is located in the proximal portion of the adapter sequence, the adapter sequence comprising a nucleic acid sequence of any one of SEQ ID NOs: 28, 30, 32, and 34. In some embodiments, the adapter sequence is a 3' adapter sequence. In some embodiments, the adapter sequence is a 5' adapter sequence. In some embodiments, the primer is not complementary to an adapter sequence that is complementary to the guide polynucleotide targeting region.

In some aspects, the disclosure provides a reaction mixture comprising: (i) a plurality of target polynucleotides, wherein the target polynucleotides comprise an adapter sequence of any one of SEQ ID NOs: 28, 30, 32, and 34-36; (ii) a predetermined concentration of a guide polynucleotide comprising a targeting region that is complementary to the adaptor sequence; and (iii) a predetermined concentration of a dCas protein or a dArgonaute protein.

In some embodiments, the predetermined concentration of the guide polynucleotide, or the dCas protein or the dArgonaute protein is lower than the concentration of target polynucleotide in the reaction mixture.

In some embodiments, the dArgonaute protein comprises LrAgo, PfAgo, TtAgo, AaAgo, AfAgo, MjAgo, MpAgo, NgAgo, RsAgo, CpAgo, IbAgo, KmAgo, or SeAgo, or a catalytically inactive variant thereof, and the guide polynucleotides are cognate to the dArgonaute protein. In some embodiments, the dCas protein comprises catalytically inactive Cpf1, C2c1, C2c3, C2c2, CasX, Cas9, or CasY, or a variant thereof, and the guide polynucleotides are cognate to the dCas protein. In some embodiments, the adapter sequence comprises a polynucleotide sequence of any one of SEQ ID NOs: 28, 30, 32, and 34-36. In some embodiments, the reaction mixture further comprises a catalytically active Cas protein or a catalytically active Argonaute protein.

In some embodiments, the disclosure provides a ribonucleoprotein (RNP) complex comprising: (i) a guide polynucleotide described herein; (ii) a Cas protein or an Argonaute protein that is cognate to the guide polynucleotide; and (iii) an adapter sequence, wherein the targeting region of the guide polynucleotide is complementary to the adapter sequence and wherein the guide polynucleotide is cognate to the Cas protein or the Argonaute protein. In some embodiments, the Argonaute protein comprises LrAgo, PfAgo, TtAgo, AaAgo, AfAgo, MjAgo, MpAgo, NgAgo, RsAgo, CpAgo, IbAgo, KmAgo, or SeAgo, or a catalytically inactive variant thereof. In some embodiments, the Cas protein comprises Cpf1, C2c1, C2c3, C2c2, CasX, Cas9, or CasY, or a catalytically inactive variant thereof. In some embodiments, the adapter sequence comprises a polynucleotide sequence of any one of SEQ ID NOs: 28, 30, 32, and 34-36.

BRIEF DESCRIPTION OF THE DRAWINGS

In FIG. 7A, a library molecule is ligated with two Y-shaped adapters at the 3' and 5' ends. In FIG. 7B, the library molecule is denatured and bound to a partial primer at the 3' end. In FIG. 7C, the bound primer is extended with a polymerase, creating a complementary strand (dashed line), which does not span the entire 3' adapter, but does comprise a double-stranded, full-length 5' adapter, which contains a PAM site for dCas9 targeting. FIG. 7D illustrates the binding of a dCas9 molecule to the double-stranded PAM site.

DETAILED DESCRIPTION

Guide Polynucleotides

Figure 1:
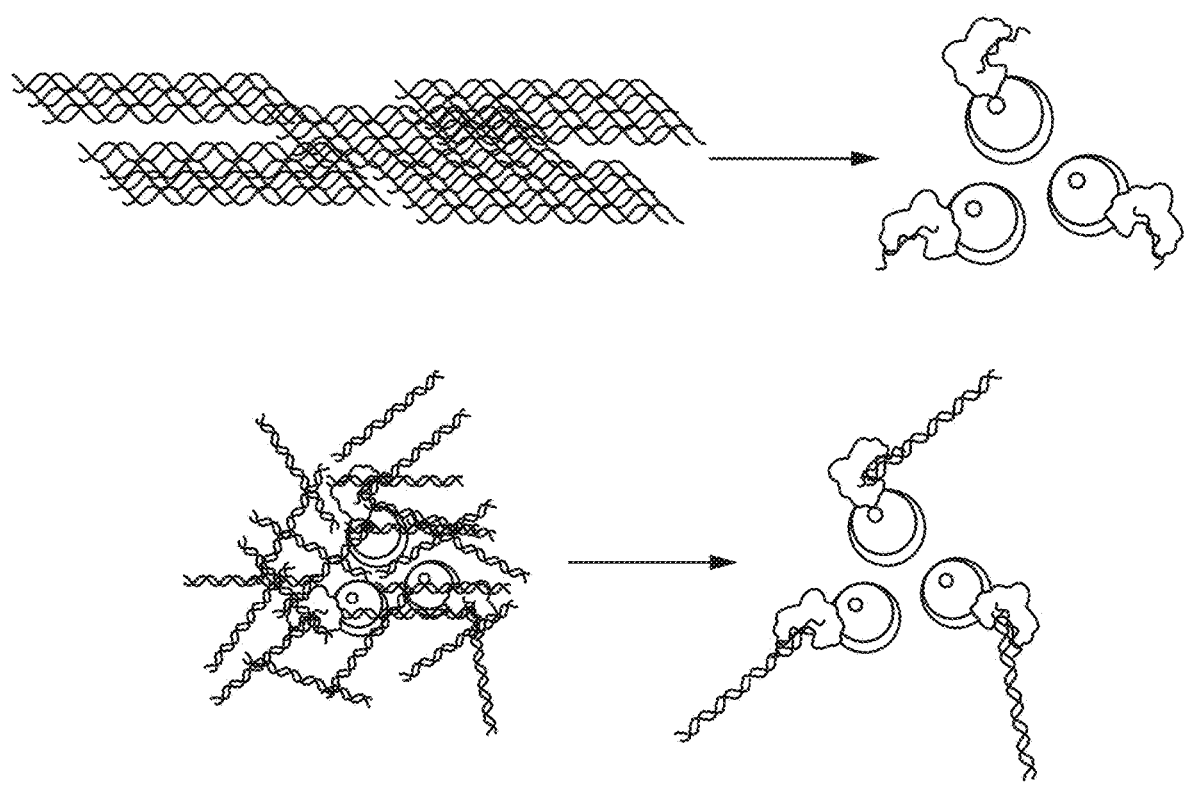
FIG. 1 shows a representative schematic of the polynucleotide capture process by a CAS-gRNA RNP bound to a metal bead.

In some aspects, this disclosure describes a guide polynucleotide comprising a targeting region that is complementary to an adapter sequence.

A "polynucleotide" refers to polymers of nucleotides (e.g., deoxyribonucleotides, ribonucleotides and modified nucleotides). The polymer may be in either single- or double-stranded form. Unless specifically limited, the term encompasses polynucleotides containing known nucleotide analogs or modified backbone residues or linkages, which are synthetic, naturally occurring, and non-naturally occurring, which have similar binding properties as the reference nucleic acid, and which are metabolized in a manner similar to the naturally occurring nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

A "guide polynucleotide" refers a polynucleotide that (1) comprises a targeting region which is complementary to a target (e.g., an adapter sequence) and (2) that is capable of facilitating binding of a ribonucleoprotein complex comprising the guide polynucleotide to the target. In some embodiments, the guide polynucleotide is a CRISPR associated protein (Cas) guide RNA (gRNA) polynucleotide or an Argonaute guide polynucleotide. In some embodiments, a Cas gRNA polynucleotide refers to a two polynucleotide system comprising a tracrRNA and a crRNA e.g., as described in Karvelis T et al., RNA Biol. 2013 May;10(5): 841-51. PMID: 23535272. The tracrRNA comprises a sequence encoding a stem loop structure that associates with the Cas protein (e.g., dCas9). The crRNA comprises a homology region that is complementary to the target (e.g., an adaptor sequence) and a region that is complementary to the tracrRNA. The crRNA and the tracrRNA may form a complex with the Cas protein, which in turn binds to a target DNA or RNA polynucleotide (depending on the Cas type). In some embodiments, a Cas gRNA polynucleotide refers to a single guide RNA (sgRNA) polynucleotide e.g., as described in Jinek M et al., Science. 2012 Aug. 17;337 (6096):816-21. doi: 10.1126/science.1225829. A sgRNA comprises a sequence encoding a stem loop structure that associates with the Cas protein and a homology region. Many Cas proteins bind to polynucleotides (e.g., double stranded DNA) in a position that is adjacent to a protospacer adjacent motif (PAM) site. In some embodiments, the homology region is complementary to a portion of the adapter sequence that is adjacent to a PAM site (e.g., sufficiently adjacent such that Cas binding to the adapter sequence can take place). Methods of making and using gRNAs are known in the art, e.g., as described in Mohr S E, et al., FEBS J. 2016 September;283(17):3232-8. PMCID: PMC5014588.

An Argonaute guide polynucleotide refers to a polynucleotide encoding a small interfering RNA (siRNA), microRNA (miRNA), P element-induced wimpy testis (PIWI)-interacting RNA (piRNA) and small interfering DNA (siDNA) e.g., as described in Wu J et al., J Adv Res. 2020 Apr 29;24:317-324, PMID: 32455006. In some embodiments, the Argonaute guide polynucleotide comprises a targeting region that is complementary to an adapter sequence as described herein. In some embodiments, a guide polynucleotide is single stranded (e.g., an RNA Cas gRNA polynucleotide). In some embodiments, a guide polynucleotide is double stranded (e.g., double stranded DNA encoding a Cas gRNA polynucleotide, or dsRNA used an Argonaute guide polynucleotide).

In some embodiments, a guide polynucleotide is an RNA molecule. In some embodiments, a guide polynucleotide is a DNA molecule. In some embodiments, the guide polynucleotide comprises modified nucleic acids (e.g., 2'F RNA, 2'OMe RNA, and/or a phosphorothioate bonds (PS)). Nucleic acids in a guide polynucleotide (e.g., an RNA guide polynucleotide like a Cas guide RNA) may be modified to increase the stability of the guide polynucleotide (e.g., reduce nuclease digestion). A Cas gRNA (e.g., a Cas9 gRNA) may comprise modified nucleic acids (e.g., 2'OMe) in regions of the gRNA that do not interact with the Cas protein (e.g., Cas9), and still maintain an ability to direct the Cas protein to the target, as described in Yin H et al., Nature Biotechnology 2017 Dec; 35(12): 1179-1187. In some embodiments, the Cas guide RNA polynucleotide comprises the modifications of the e-sgRNA as described in Yin et al. 2017. In some embodiments, a Cas9 sgRNA does not comprise a modified nucleic acid (e.g., a 2'OH modification) at one or more positions 22-27, 43-45, 47, 49, 51, 58, 59, 62, 63-65, 68-69, or 82 counted from the 5' end of the sgRNA (i.e., with reference to an sgRNA of

```
(GGGCGAGGAGCUGUUCACCGGUUUUAGAGCUAGAAAUAGCAAGUUAAAA

UAAGGCUAGUCCGUUAUCAACUUGAAAAAGUGGCACCGAGUCGGUGCUUU

UU, SEQ ID NO: 46)).
```

In some embodiments, the sgRNA comprises 2'-O-methyl RNA bases. In 2'-O-methyl RNA bases, the 2'-hydroxyl (—OH) group of the ribose sugar in the RNA molecule is replaced by a methyl group (—CH3). This modification affects the ribose sugar, and the nitrogenous bases (adenine, guanine, cytosine, uracil) themselves are not typically modified in this context. The 2'-O-methyl RNA bases are 2'O-methyladenosine, 2'O-methylguanosine, 2'O-methylcytidine, and 2'O-methyluridine. In some embodiments, the sgRNA comprises the sequence:

```
                                          (SEQ ID NO: 48)
5'-mA*mG*mA* rUrCrG rGrArA rGrArG rCrGrU rCrGrU rGrUrG rUrUrU rUrArG rArGrCrUrArG rArArA rUrArG rCrArA rGrUrU rArArA rArUrA rArGrG rCrUrA rGrUrC rCrGrU rUrArU rCrArA rCrUrU rGrArA rArArA rGrUrG rGrCrA rCrCrG rArGrU rCrGrG rUrGrC mU*mU*mU*rU-3'
``` where mA and mG are 2'-O-methyladenosine, 2'O-methylguanosine RNA bases.

A "targeting region" of a guide polynucleotide refers to a region of the guide polynucleotide that is complementary to a target polynucleotide sequence (e.g., an adapter sequence). In some embodiments, the guide polynucleotide is a Cas gRNA polynucleotide comprising a homology region. A Cas gRNA polynucleotide homology region may comprise a series of contiguous amino acids that are complementary to a target polynucleotide sequence (e.g., an adapter sequence). In some embodiments, the homology region is 15, 16, 17, 18, 19, 20, 21, 22, 23, 24, 25, 26, 27, 28, 29, 30 or more nucleotides in length. In some embodiments, the homology region is 18-26 nucleotides in length. In some embodiments, the homology region is 17-24 nucleotides in length. In some embodiments, the homology region is 18-22 nucleotide in length. In some embodiments, the homology region is 20 nucleotides in length.

In some embodiments, the guide polynucleotide is an Argonaute guide polynucleotide. Argonaute guide polynucleotides may be RNA interference (RNAi) polynucleotides. In some embodiments, the Argonaute guide polynucleotide comprises a targeting region of a small interfering RNA (siRNA), microRNA (miRNA), P element-induced wimpy testis (PIWI)-interacting RNA (piRNA) and small interfering DNA (siDNA) e.g., as described in Wu J et al., J Adv Res. 2020 Apr. 29;24:317-324, PMID: 32455006.

In some embodiments, the targeting region is complementary to an adapter sequence as described herein. In some embodiments, the targeting region is complementary to a static region (e.g., that generally does not change between adapters) of the adapter sequence. In some embodiments, the targeting region is complementary to a sequence comprising a region that was added to the sequence for the purpose of being complementary to a guide polynucleotide targeting region. For example, an additional sequence can be added to an adaptor sequence for the purpose of being complementary to a guide polynucleotide targeting region (e.g., for use in library normalization). Such an additional sequence may be a sequence that is specifically bound by a Cas protein-gRNA complex or an Argonaute guide polynucleotide complex compared to other sequences in a polynucleotide sequencing library.

In some embodiments, the targeting region is complementary to a next-generation sequencing adapter sequence. In some embodiments, the static region is a static region of a next-generation sequencing adapter sequence. In some embodiments, the targeting region is complementary to a p5 adapter or a p7 adapter. In some embodiments, the p5 adapter and the p7 adapter are ILLUMINA sequencing adapters. In some embodiments, the targeting region is complementary to an i5 polynucleotide sequence of SEQ ID NO: 27 or SEQ ID NO: 28. In some embodiments, the targeting region is complementary to an i7 adapter sequence of SEQ ID NO: 29 or SEQ ID NO: 30. In some embodiments, the targeting region is complementary to a NEXTERA Read 1 Adapter (e.g., SEQ ID NO: 31 or SEQ ID NO: 32) or a NEXTERA Read 2 Adapter (e.g., SEQ ID NO: 33 or SEQ ID NO: 34). In some embodiments, the targeting region is complementary to an ION TORRENT A Adapter or an ION TORRENT P1 Adapter. In some embodiments, the targeting region is complementary to an ION TORRENT A Adapter of SEQ ID NO: 35. In some embodiments, the targeting region is complementary to a ION TORRENT P1 Adapter of SEQ ID NO: 36. In some embodiments, the gRNA polynucleotide comprises a homology region of any one of SEQ ID NOs: 1-26. In some embodiments, the gRNA polynucleotide comprises a homology region of SEQ ID NO: 1.

The term "complementary" as used herein refers to the degree of expected Watson-crick base pairing between a first polynucleotide (e.g., a guide polynucleotide targeting region) and a second polynucleotide (e.g., an adaptor sequence). Complementary nucleotides are, generally, A and T (or A and U), and G and C. In some embodiments, complementary refers to 100% complementarity between two polynucleotides (e.g., a guide polynucleotide targeting region and an adapter sequence). In some embodiments, complementary refers to 70%, 80%, 90%, 95%, or 99% complementarity between two polynucleotides. For example, a targeting region may be complementary to an adapter sequence when one, two, or three nucleic acids in the targeting region are not complementary to the adapter sequence. In some embodiments, complementary refers to a sufficiently degree of Watson-crick base pairing between a guide polynucleotide targeting region (of a RNP (e.g., dCas9 bound to a guide RNA) and an adaptor sequence for the RNP to bind to the adaptor sequence. In some embodiments, complementary refers to a sufficient degree of Watson Crick base pairing between an Argonaute guide polynucleotide (e.g., a miRNA, siRNA, pwRNA, shRNA, or siDNA) and a target sequence (e.g., an adapter sequence) to direct binding of an Argonaute protein comprising the Argonaute guide polynucleotide to bind to the target.

An "adapter sequence" refers to a polynucleotide added (e.g., ligated) to an end (e.g., 3' and/or 5') of a target polynucleotide for use in sequencing of the polynucleotide. In some embodiments, the adapter sequence refers to a sequence of nucleic acids encoding the adapter. In some embodiments, the adapter sequence may be used for sequencing using a particular sequencing platform. For example, ILLUMINA i5/p5 and i7/p7 adapter sequences may be used for sequencing using the ILLUMINA sequencing platform. In some embodiments, the adapter sequence comprises a static region (e.g., that generally does not change between adapters) and a dynamic region (e.g., that may change between adapters). In some embodiments, the adapter sequence comprises a distal region (generally static), an index region (generally dynamic), and a proximal region (generally static). For example, an ILLUMINA adapter sequence may comprise a p5 region which is static, an index region which is dynamic, and an i5 region which is static. In some embodiments, the guide polynucleotide targeting region is complementary to a static region of the adapter sequence. In some embodiments, the guide polynucleotide targeting region is complementary to the dynamic region of the adapter sequence. In some embodiments, the guide polynucleotide comprises a targeting region that is complementary to a static region of an adapter sequence (e.g., a distal region or a proximal region of an adapter sequence). In some embodiments, the guide polynucleotide comprises a targeting region that is complementary to a dynamic region of an adapter sequence (e.g., an index). In some embodiments, at least some of the target polynucleotides comprise the same static adapter sequences (e.g., the same distal and/or proximal region). In some embodiments, the majority of the target polynucleotide comprise the same static adapter sequence. In some embodiments, all of the target polynucleotides comprise the same static adapter sequence.

In some embodiments, the adapter sequence is modified to comprise a Cas protein protospacer-adjacent motif (PAM) or a reverse complement of a PAM. A "protospacer-adjacent motif (PAM)" is a nucleotide motif (often 3 consecutive nucleotides in the polynucleotide) that is required for Cas protein binding to the target polynucleotide. The canonical Cas9 PAM sequence is 5'-NGG, wherein N is any nucleotide A, G, C, or T. In some embodiments, the adapter sequence is modified to comprise a PAM or reverse complement of a PAM to facilitate binding of the Cas-gRNA complex to the target polynucleotide. For example, a PAM sequence may be added to the 3' end or 5' end of the adapter sequence. In some embodiments, a distal sequence can be modified to comprise a protospacer-adjacent motif (PAM) or a reverse complement thereof.

In some embodiments, the adaptor sequence is an adapter sequence used IN ILLUMINA, ION TORRENT, PACBIO, ELEMENT, ULTIMA, OMNIOME, SINGULAR, or MGI sequencing. In some embodiments, the adapter sequence is an adapter sequence from any one of the following kits: a WATCHMAKER DNA Library Prep Kit with Fragmentation or WATCHMAKER RNA Library Prep Kit with Polaris Depletion ILLUMINA TruSeq PCR-Free Library Preparation Kit, TruSeq Nano DNA Library Prep Kit, NEXTERA DNA Library Prep Kit, NEXTERA DNA XT Library Prep Kit, NEXTERA Rapid Capture Exome Kit, NEXTERA Rapid Capture Expanded Exome Kit, AmpliSeq for ILLUMINA Library Prep Kit, ILLUMINA RNA Prep with Enrichment Kit, ILLUMINA Stranded mRNA Prep Kit, TruSeq RNA Library Prep Kit, TruSeq Stranded Total RNA Kit, TruSeq Stranded mRNA Kit, TruSeq Small RNA Kit. In some embodiments, the adaptor sequence is an adapter sequence used in any one of the following kits: NEBNEXT Fast DNA for ION TORRENT, NEBNEXT Fast DNA Fragmentation & Library Prep Set for ION TORRENT, THERMOFISHER Precision ID Library Kit, THERMOFISHER Ion Xpress Plus Fragment Library Kit, THERMOFISHER Ion Xpress Barcode Adapters 1-96 Kit, and/or THERMOFISHER Ion AmpliSeq Transcriptome Human Gene Expression Kit. In some embodiments, the adaptor sequence is an adapter sequence used in any one of the following kits: a PACBIO SMRTbell Template Prep Kit 1.0, SMRTbell Barcoded Adapter Complete Prep Kit-96, or Barcoded Adapter Kit. In some embodiments, the targeting region may be complementary an adaptor sequence used in QIAGEN QIAseq Stranded RNA Library Kit or QIAseq UPX 3' Transcriptome Kit, a Perkin Elmer NEXTFLEX Rapid Directional RNA-Seq Kit or NEXTFLEX Small RNA-Seq Kit, or a Takara Bio SMART-Seq mRNA Kit or SMART-Seq mRNA LP Kit.

In some embodiments, the adapter sequence comprises a shared Y-adapter sequence. In certain embodiments, the shared Y-adapter sequence is a 13 bp sequence. In other embodiments, the shared Y-adapter sequence is a 6, 7, 8, 9, 10, 11, 12, 14, 15, 16, 17, 18, 19, 20, 21, 22, 23, 24, 25, 26, 27, 28, 29, or 30 bp sequence.

In some embodiments, the adapter sequence may comprise a sequence of any one of SEQ ID NOs: 27-36.

Kits

In some aspects, this disclosure describes a kit comprising: (a) a guide polynucleotide described herein; and (b) a Cas protein or an Argonaute protein, or a polynucleotide sequence encoding a Cas protein or an Argonaute protein (e.g., as described herein).

In some embodiments, the kit comprises a Cas protein. A "Cas protein" refers to a Clustered Regularly Interspaced Short Palindromic Repeats (CRISPR)-associated protein. In some embodiments, the Cas protein has nuclease activity. In some embodiments, the Cas protein does not have nuclease activity (dCas). In some embodiments, the Cas protein has nicking activity (nickase).

In some embodiments, the Cas protein is a Cas9 protein. "Cas9" refers to a Cas9 protein or a fragment thereof present in any bacterial species that encodes a Type II CRISPR/Cas9 system. See, for example, Makarova et al., Nature Reviews, Microbiology, 9: 467-477 (2011), including supplemental information. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chloroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi et al., 2013, RNA Biol. 10(5): 726-37; Hou et al., 2013, Proc. Natl. Acad. Sci. USA 110(39):15644-49; Sampson et al., 2013, 497(7448):254-57; and Jinek et al., 2012, Science 337(6096):816-21. Full-length Cas9 is an RNA-mediated endonuclease comprising a recognition domain and two nuclease domains (HNH and RuvC, respectively). In the amino acid sequence, HNH is linearly continuous, whereas RuvC is separated into three regions, one left of the recognition domain, and the other two right of the recognition domain flanking the HNH domain. Cas9 from *Streptococcus pyogenes* is targeted to a genomic site in a cell by interacting with a guide RNA that hybridizes to a 20-nucleotide DNA sequence that immediately precedes an NGG motif recognized by Cas9.

In some embodiments, the Cas9 is a catalytically-inactive or nuclease-dead Cas9 (dCas9) that has been modified to inactivate Cas9 nuclease activity. Modifications include, but are not limited to, altering one or more amino acids to inactivate the nuclease activity or the nuclease domain. For example, and not to be limiting, D10A, H840A, and/or R1335K mutations can be made in Cas9 from *Streptococcus pyogenes* to inactivate Cas9 nuclease activity. In some embodiments, the Cas9 protein comprises a D10A mutation and a H840A mutation. Other modifications include removing all or a portion of the nuclease domain of Cas9, such that the sequences exhibiting nuclease activity are absent from Cas9. Accordingly, a catalytically-inactive Cas9 may include polypeptide sequences modified to inactivate nuclease activity or removal of a polypeptide sequence or sequences to inactivate nuclease activity. The catalytically-inactive Cas9 retains the ability to bind to DNA even though the nuclease activity has been inactivated. Accordingly, dCas9 includes the polypeptide sequence or sequences required for DNA binding but includes modified nuclease sequences or lacks nuclease sequences responsible for nuclease activity.

In some embodiments, the catalytically-inactive Cas9 protein is a full-length Cas9 sequence from *S. pyogenes* lacking the polypeptide sequence of the RuvC nuclease domain and/or the HNH nuclease domain and retaining the DNA binding function. In other embodiments, the catalytically-inactive Cas9 protein sequences have at least 30%, 40%, 50%, 60%, 70%, 80%, 90%, 95%, 98% or 99% identity to Cas9 polypeptide sequences lacking the RuvC nuclease domain and/or the HNH nuclease domain and retains DNA binding function. In some embodiments, the Cas protein is Alt-RTM S.p. dCas9 Protein V3 (IDT).

In some embodiments, the Cas protein is a Cpf1 (Cas12a), C2c1, C2c3, C2c2, CasX, or CasY protein. In some embodiments, the Cas protein has been modified to inactivate Cas9 nuclease activity. Modifications include, but are not limited to, altering one or more amino acids to inactivate the nuclease activity or the nuclease domain of the Cas protein. For example, D908, D832, E993, R1226, and/or D1235 mutations can be made in Cpf1 from *Acidaminacoccus* sp. BV3L6, Lachnospiraceae ND2006, or *Francisella tularensis* subsp. *novicida* U112, to inactivate Cpf1 nuclease activity. Other modifications include removing all or a portion of the nuclease domain, such that the sequences exhibiting nuclease activity are absent. Accordingly, a catalytically-inactive Cas protein may include polypeptide sequences modified to inactivate nuclease activity or removal of a polypeptide sequence or sequences to inactivate nuclease activity. The catalytically-inactive Cas protein retains the ability to bind to DNA even though the nuclease activity has been inactivated. Accordingly, catalytically-inactive Cas protein includes the polypeptide sequence or sequences required for DNA binding but includes modified nuclease sequences or lacks nuclease sequences responsible for nuclease activity. In some embodiments, the catalytically-inactive Cas protein is a full-length Cas sequence lacking the polypeptide sequence of the nuclease domain and retaining the DNA binding function. In other embodiments, the catalytically-inactive Cas protein sequences have at least 30%, 40%, 50%, 60%, 70%, 80%, 90%, 95%, 98% or 99% identity to Cas polypeptide sequences lacking the nuclease domain and retains DNA binding function.

In some embodiments, the Cas protein comprises an amino acid sequence having at least 95% identity to SEQ ID NO: 37 or SEQ ID NO: 38. In some embodiments, the Cas protein comprises an amino acid sequence of SEQ ID NO: 37 or SEQ ID NO: 38.

In some embodiments, the dCas protein comprises an amino acid sequence having at least 95% identity to SEQ ID NO: 37. In some embodiments, the dCas protein comprises an amino acid sequence of SEQ ID NO: 37.

In some embodiments, the Cas protein comprise a nuclease localization sequence.

In some embodiments, the kit comprising an Argonaute protein. An "Argonaute protein" refers to a protein that binds small noncoding nucleic acids (e.g., an Argonaute guide polynucleotide) and utilizes them for the guided cleavage of complementary nucleic acid targets or indirect gene silencing by recruiting additional factors. Catalytically-active Argonaute proteins are capable of nucleic acid guided binding to a complementary nucleic acid target (e.g., DNA) and cleavage of the nucleic acid target. See, e.g., Kaya et al., 2016, PNAS 113(5):4057-62. The prokaryotic Argonaute (AGO) gene family encodes several domains: N-terminal (N), PAZ, MID, and a C-terminal PIWI domain. The MID and PAZ domains are responsible for binding of the 5'-end and 3'-end, respectively, of a guide polynucleotide. In contrast to eukaryotic Agos that use exclusively small RNA guides, the majority of characterized prokaryotic Agos bind single-stranded DNA (ssDNA) guides. The Ago PIWI domain comprises nuclease activity. In some embodiments, the Argonaute protein is catalytically-inactive. In some embodiments, the Argonaute protein is a CbAgo protein that is catalytically-inactive. In some embodiments, the Argonaute protein is a LrAgo, PfAgo, TtAgo, AaAgo, AfAgo, MjAgo, MpAgo, NgAgo, RsAgo, CpAgo, IbAgo, KmAgo, or SeAgo protein that is catalytically-inactive. In certain embodiments, the Argonaute protein has been modified to inactivate nuclease activity or inherently has reduced nuclease activity (see, e.g., Kaya et al., 2016, PNAS 113(5):4057-62). Modifications may include, but are not limited to, altering one or more amino acids to inactivate the nuclease activity or the nuclease domain of the Argonaute protein. For example, in some embodiments, the catalytically-inactive Argonaute protein is a CbAgo protein that comprises a D541A mutation and a D611A mutation. See, e.g., Hegge et al., 2019, Nuc. Acids Res. 47(11):5809-21. Alternatively, all or a portion of the nuclease domain may be removed, such that the sequences exhibiting nuclease activity are absent. Accordingly, a catalytically-inactive Argonaute protein may include polypeptide sequences modified to inactivate nuclease activity or removal of a polypeptide sequence or sequences to inactivate nuclease activity. The catalytically-inactive Argonaute protein retains the ability to bind to DNA even though the nuclease activity has been inactivated. Accordingly, catalytically-inactive Argonaute protein includes the polypeptide sequence or sequences required for DNA binding but includes modified nuclease sequences or lacks nuclease sequences responsible for nuclease activity. In some embodiments, the catalytically-inactive Argonaute protein is a full-length Argonaute sequence lacking the polypeptide sequence of the nuclease domain and retaining the DNA binding function. In other embodiments, the catalytically-inactive Argonaute protein sequences have at least 30%, 40%, 50%, 60%, 70%, 80%, 90%, 95%, 98% or 99% identity to the Argonaute polypeptide sequences lacking the nuclease domain and retains DNA binding function.

In some embodiments, the dArgonaute protein comprises an amino acid sequence having at least 95% identity to any one of SEQ ID NOs: 40-45. In some embodiments, the dArgonaute protein comprises an amino acid sequence of any one of SEQ ID NOs: 40-45.

In some embodiments, the kit comprises a catalytically inactive Cas protein (dCas protein) or a catalytically inactive Argonaute protein (e.g., dArgonaute) as described herein. In some embodiments, the kit comprises a catalytically inactive Cas protein (dCas protein) and a catalytically active Cas protein as described herein. In some embodiments, the kit comprises a catalytically a catalytically inactive Argonaute protein (e.g., dArgonaute) a catalytically active Argonaute protein as described herein. In some embodiments, the kit comprises a dCas and a cognate dCas guide RNA polynucleotide. In some embodiments, the kit comprises a dCas9 and a cognate dCas9 guide RNA. In some embodiments, the kit comprises a dArgonaute and a cognate dArgonaute guide polynucleotide.

In some embodiments, the kit comprises a Cas protein comprising an affinity tag or a Argonaute protein comprising an affinity tag. In some embodiments, the affinity tag is Albumin-binding protein (ABP), Alkaline Phosphatase (AP), AU1 epitope, AU5 epitope, Bacteriophage T7 epitope (T7-tag), Bacteriophage V5 epitope (V5-tag), Biotin-carboxy carrier protein (BCCP), Bluetongue virus tag (B-tag), Calmodulin binding peptide (CBP), Chloramphenicol Acetyl Transferase (CAT), Cellulose binding domain (CBP), Chitin binding domain (CBD), Choline-binding domain (CBD), Dihydrofolate reductase (DHFR), E2 epitope, FLAG epitope, Galactose-binding protein (GBP), Green fluorescent protein (GFP), Glu-Glu (EE-tag), Glu-Glu (EE-tag), Human influenza hemagglutinin (HA), HaloTag®, Histidine affinity tag (HAT), Horseradish Peroxidase (HRP), HSV epitope, Ketosteroid isomerase (KSI), KT3 epitope, LacZ, Luciferase, Maltose-binding protein (MBP), Myc epitope, Nus, PDZ domain, PDZ ligand, Polyarginine (Arg-tag), Polyaspartate (Asp-tag), Polyhistidine, (His-tag), Polyphenylalanine (Phe-tag), Profinity eXact, Protein C, S1-tag, S-tag, Streptavadin-binding peptide (SBP), Staphylococcal protein A (Protein A), Staphylococcal protein G (Protein G), Strep-tag, Streptavadin, Small Ubiquitin-like Modifier (SUMO), Tandem Affinity Purification (TAP), T7 epitope, Thioredoxin (Trx), TrpE, Ubiquitin, Universal, and VSV-G as described in Kimple M E et al., Curr Protoc Protein Sci. 2013 Sep 24;73:9.9.1-9.9.23. doi: 10.1002/0471140864.ps0909s73.

In some embodiments, the affinity tag and corresponding affinity tag binding molecule, in a kit or for use in the method, are selected from Table 1.

TABLE 1

Affinity tag and affinity tag binding molecule.

| Affinity tag | Fusion MW | Affinity tag binding molecule |
|---|---|---|
| GST | 27 kDa | Glutathione beads |
| Protein A | 49 kDa | IgG-conjugated beads |
| Protein G | 65 kDa | IgG-conjugated beads |
| Streptavidin | 16.5 kDa | Biotin beads |
| Biotin | post-translational | Streptavidin beads |
| Cell Surface Vimentin (CSV) | 57 kDa | CSV monoclonal Ab beads |
| Human PSMA | 82.5 kDa | PMSA monoclonal Ab beads |
| IgG Fc heavy chain | ~25-50 kDa | Protein A/G beads |

TABLE 1-continued

Affinity tag and affinity tag binding molecule.

| Affinity tag | Fusion MW | Affinity tag binding molecule |
|---|---|---|
| Chitin binding domain | 27 kDa | Chitin beads |
| Maltose binding protein (MBP) | 42.5 kDa | Amylose or anti-MBP beads |
| Protein L 'B' repeats | 36 kDa | IgG-conjugated beads |

In some embodiments, the kit comprises a guide polynucleotide that is capable of binding to the Cas protein (e.g., cognate the guide polynucleotide is cognate to the Cas protein) or the Argonaute protein of the kit to form a ribonucleoprotein complex and the ribonucleoprotein complex is capable of binding to an adapter sequence.

The term "cognate" as used in the context of the guide polynucleotide and the Cas protein or Argonaute protein refers to a guide polynucleotide that is compatible with the Cas protein or the Argonaute protein (e.g., the guide polynucleotide is capable of directing the Cas protein or the Argonaute protein to a target polynucleotide). For example, a Cas9 sgRNA is cognate to Cas9 and dCas9.

The terms "binds" or "specifically binds," and like terms, refer to a molecule (e.g., a Cas-gRNA complex or a Argonaute-guide polynucleotide complex) that binds to a target nucleic acid with at least 2-fold greater affinity than non-target nucleic acids, e.g., at least any of 2-fold, 3-fold, 4-fold, 5-fold, 6-fold, 7-fold, 8-fold, 9-fold, 10-fold, 20-fold, 25-fold, 50-fold, 100-fold, 1,000-fold, 10,000-fold, or greater affinity for the target nucleic acid compared to an unrelated nucleic acid when assayed under the same binding affinity assay conditions. In some embodiments, the term "binds" or "specifically binds," as used herein, can be exhibited, for example, by a molecule (e.g., a Cas-gRNA complex or a Argonaute-guide polynucleotide complex) having an equilibrium dissociation constant KD for the target nucleic acid of, e.g., 10 -2 M or smaller, e.g., $10^{-3}$ M, $10^{-4}$ M, $10^{-5}$ M, $10^{-6}$ M, $10^{-7}$ M, $10^{-8}$ M, $10^{9}$ M, $10^{-10}$M, $10^{-11}$ M, or $10^{-12}$ M. In some embodiments, an antibody has a KD of less than 10 nM or less than 100 nM.

In some embodiments, the kit further comprises a primer that is complementary to a portion of an adapter sequence (e.g., as described herein). In some embodiments, the primer is complementary to a proximal portion of an adapter sequence. This primer may be used for creating double stranded target nucleotides comprising a double stranded proto-spacer adjacent motif (PAM) site that a dCas protein (e.g., as described herein) can use for binding. In some embodiments, the primer binds to a proximal portion of the adapter sequences such that the new polynucleotide (which is complementary to the target polynucleotide) does not comprise the distal portion of the adapter sequence and thus cannot be sequenced using next-generation sequencing (e.g., ILLUMINA Sequencing). Without being bound to theory, this method may be advantageous compared to PCR based methods because errors (e.g., mutations) introduced during elongation of the primer are not sequenced, but double stranded target polynucleotides may still be produced and bound be dCas proteins.

In some embodiments, the primer is a DNA primer. In some embodiments, the DNA primer comprises nucleic acid modifications (e.g., as described herein). In some embodiments, the portion of the adapter sequence is located in the proximal portion of the adapter sequence. In some embodiments, the proximal portion of the adapter sequence comprises a nucleic acid sequence of any one of SEQ ID NOs:

28, 30, 32, and 34. In some embodiments, the primer is complementary to a 3' adapter sequence. In some embodiments, the primer is complementary to a 5' adapter sequence. In some embodiments, the primer is not complementary to an adapter sequence that is complementary to the guide polynucleotide targeting region. In some embodiments, the primer when bound to the adapter sequence and elongated does not elongate the entire adapter sequence.

Reaction Mixtures

In some aspects, this disclosure describes a reaction mixture comprising: (i) a plurality of target polynucleotides, wherein the target polynucleotides comprise an adapter sequence; (ii) a predetermined concentration of a guide polynucleotide comprising a targeting region that is complementary to the adaptor sequence; and (iii) a predetermined concentration of a dCas protein or a dArgonaute protein. In some embodiments, the reaction mixture comprises an p aqueous solution (e.g., a buffer that is suitable for performing a method described herein). In some embodiments, the reaction mixture comprises a predetermined concentration of dCas9 protein). In some embodiments, the reaction mixture comprises a predetermined concentration of dArgonaute protein. In some embodiments, the reaction mixture comprises target polynucleotides comprising an adapter sequence of any one of SEQ ID NOs: 27-36. In some embodiments, the reaction mixture comprises a predetermined concentration of a guide polynucleotide of any one of SEQ ID NOs: 27-36.

In some embodiments, the reaction mixture comprises a plurality of target polynucleotides comprising an adapter sequence at a concentration of 50 femtomoles (fmols) to 3,400 fmols. In some embodiments, the reaction mixture comprises a plurality of target p polynucleotides comprising an adapter sequence at a concentration of 200 fmols to 3,400 fmols. In some embodiments, the reaction mixture comprises a plurality of target polynucleotides comprising an adapter sequence at a concentration of 300 fmols to 3,400 fmols. In some embodiments, the reaction mixture comprises a plurality of target polynucleotides comprising an adapter sequence at a concentration of 500 fmols to 3,400 fmols. In some embodiments, the 5 reaction mixture comprises a plurality of target polynucleotides comprising an adapter sequence at a concentration of 750 fmols to 3,400 fmols. In some embodiments, the reaction mixture comprises a plurality of target polynucleotides comprising an adapter sequence at a concentration of 1,000 fmols to 3,400 fmols. In some embodiments, the reaction mixture comprises a plurality of target polynucleotides comprising an adapter sequence at a concentration of 1,000 fmols to 3,400 fmols. In some embodiments, the reaction mixture comprises a plurality of target polynucleotides comprising an adapter sequence at a concentration of 2,000 fmols to 3,400 fmols. In some embodiments, the reaction mixture comprises a plurality of target polynucleotides comprising an adapter sequence at a concentration of 50 fmols. In some embodiments, the reaction mixture comprises a plurality of target polynucleotides comprising an adapter sequence at a concentration of 3,400 fmols. In some embodiments, the reaction mixture comprises a plurality of target polynucleotides comprising an adapter sequence at a concentration of 500 fmols to 3,400 fmols.

In some embodiments, the reaction mixture comprises a predetermined concentration of dCas9 of SEQ ID NO: 38, target polynucleotides comprising an adapter sequence of SEQ ID NO: 28, and a predetermined concentration of a guide polynucleotide (e.g., an RNA guide polynucleotide) that comprises a homology region that is complementary to the adapter sequence (e.g., the homology region comprises SEQ ID NO: 37).

In some embodiments, the reaction mixture comprises a predetermined concentration of dArgonaute of any one of SEQ ID NOs: 40-45 (e.g., a catalytically inactive variant of any one of SEQ ID NOs: 40-45), target polynucleotides comprising an adapter sequence of SEQ ID NO: 28, and a predetermined concentration of a dArgonaute guide polynucleotide that comprises a targeting region which is complementary to the adapter sequence.

In some embodiments, the reaction mixture further comprises a catalytically active nuclease as described herein.

Ribonucleoprotein (RNP) Complexes

In some aspects this disclosure provides a ribonucleoprotein (RNP) complex comprising: (i) a guide polynucleotide; (ii) a Cas protein (e.g., dCas) or an Argonaute protein (e.g., dArgonaute); and (iii) an adapter sequence; wherein the targeting region of the guide polynucleotide is complementary to the adapter sequence.

In some embodiments, the RNP complex comprises (i) a RNA Cas gRNA polynucleotide (ii) a Cas protein as described herein, and (iii) an adapter sequence; wherein the homology region of the RNA Cas gRNA polynucleotide is complementary to the adapter sequence.

In some embodiments, the RNP complex comprises (i) a RNA Cas gRNA polynucleotide comprising a homology region of any one of SEQ ID NOs: 1-26 (ii) a dCas protein of SEQ ID NO: 37, and (iii) an adapter sequence of any one of SEQ ID NOs: 27-36; wherein the homology region of the RNA Cas gRNA polynucleotide is complementary to the adapter sequence.

In some embodiments, the RNP complex comprises (i) a RNA Cas gRNA polynucleotide comprising a homology region of any one of SEQ ID NO: 1 (ii) a dCas protein of SEQ ID NO: 37, and (iii) an adapter sequence of any one of SEQ ID NOs: 28; wherein the homology region of the RNA Cas gRNA polynucleotide is complementary to the adapter sequence.

In some embodiments, the RNP complex comprises (i) an Argonaute guide polynucleotide(ii) an Argonaute protein, and (iii) an adapter sequence; wherein the targeting region of the Argonaute guide polynucleotide is complementary to the adapter sequence.

In some embodiments, the RNP complex comprises (i) an Argonaute guide polynucleotide (e.g., an siDNA) (ii) an Argonaute protein of any one of SEQ ID NOs: 39-45 and (iii) an adapter sequence of SEQ ID NO: 28; wherein the targeting region of the Argonaute guide polynucleotide is complementary to the adapter sequence.

In some embodiments, the RNP complex comprises (i) an Argonaute guide polynucleotide (e.g., an siDNA) (ii) an Argonaute protein of any one of SEQ ID NOs: 40-45 and (iii) an adapter sequence of SEQ ID NO: 28; wherein the targeting region of the Argonaute guide polynucleotide is complementary to the adapter sequence.

In some embodiments of RNP complexes provided herein, the adapter sequence is unmodified. In some embodiments, the adapter sequence is unmodified at the 5' end.

In some embodiments, the RNP complexes are present at a concentration of 250 femtomoles (fmols) to 14,000 fmols. In some embodiments, the RNP complexes are present at a concentration of 300 fmols to 14,000 fmols. In some embodiments, the RNP complexes are present at a concentration of 2,000 fmols to 14,000 fmols. In some embodiments, the RNP complexes are present at a concentration of 6,000 fmols to 14,000 fmols. In some embodiments, the RNP complexes are present at a concentration of 10,000 fmols to 14,000 fmols. In some embodiments, the RNP complexes are present at a concentration of at least 250 fmols . In some embodiments, the RNP complexes are present at a concentration of at least 300 fmols. In some embodiments, the RNP complexes are present at a concentration of at least 2,000 fmols. In some embodiments, the RNP complexes are present at a concentration of at least 6,000 fmols. In some embodiments, the RNP complexes are present at a concentration of at least 10,000 fmols. In some embodiments, the RNP complexes are present at a concentration of 250 fmols. In some embodiments, the RNP complexes are present at a concentration of 300 fmols. In some embodiments, the RNP complexes are present at a concentration of 2,000 fmols. In some embodiments, the RNP complexes are present at a concentration of 6,000 fmols. In some embodiments, the RNP complexes are present at a concentration of 10,000 fmols. In some embodiments, the RNP complexes are present at a concentration of 14,000 fmols.

Sequences

TABLE 2

| SEQ ID NO | Description | Sequence |
|---|---|---|
| 1 | ILLUMINA i5 gRNA-1 polynucleotide homology region | GAUCGGAAGAGCGUCGUGUA |
| 2 | ILLUMINA i5 gRNA-2 polynucleotide homology region | AGAUCGGAAGAGCGUCGUGU |
| 3 | ILLUMINA i5 gRNA-3 polynucleotide homology region | AGCGUCGUGUAGGGAAAGAG |
| 4 | ILLUMINA i5 gRNA-4 polynucleotide homology region | AGAGCGUCGUGUAGGGAAAG |
| 5 | ILLUMINA i5 gRNA-5 polynucleotide homology region | GAAGAGCGUCGUGUAGGGAA |
| 6 | ILLUMINA i5 gRNA-6 polynucleotide homology region | AUCGGAAGAGCGUCGUGUAG |
| 1 | ILLUMINA i5 gRNA-7 polynucleotide homology region | GAUCGGAAGAGCGUCGUGUA |
| 2 | ILLUMINA i5 gRNA-8 polynucleotide homology region | AGAUCGGAAGAGCGUCGUGU |
| 9 | ILLUMINA i7 gRNA-1 polynucleotide homology region | AGUUCAGACGUGUGCUCUUC |
| 10 | ILLUMINA i7 gRNA-2 polynucleotide homology region | GUGACUGGAGUUCAGACGUG |
| 11 | NEXTERA Read 1 gRNA-1 polynucleotide homology region | CACAUCUGAGACGCUGCCGA |
| 12 | NEXTERA Read 1 gRNA-2 polynucleotide homology region | AUACACAUCUGAGACGCUGC |

TABLE 2-continued

Sequences

| SEQ ID NO | Description | Sequence |
|---|---|---|
| 13 | NEXTERA Read 2 gRNA-1 polynucleotide homology region | GGCUCGGAGAUGUGUAUAAG |
| 14 | NEXTERA Read 2 gRNA-2 polynucleotide homology region | UGGGCUCGGAGAUGUGUAUA |
| 15 | NEXTERA Read 2 gRNA-3 polynucleotide homology region | GGGCUCGGAGAUGUGUAUAA |
| 16 | NEXTERA Read 2 gRNA-4 polynucleotide homology region | GUGGGCUCGGAGAUGUGUAU |
| 17 | Ion Torrect A adapter gRNA-1 homology region | GGAGACACGCAGGGAUGAGA |
| 18 | Ion Torrect A adapter gRNA-2 homology region | AGUCGGAGACACGCAGGGAU |
| 19 | Ion Torrect A adapter gRNA-3 homology region | GAGACACGCAGGGAUGAGAU |
| 17 | Ion Torrect A adapter gRNA-4 homology region | GGAGACACGCAGGGAUGAGA |
| 21 | Ion Torrect A adapter gRNA-5 homology region | GUCGGAGACACGCAGGGAUG |
| 22 | Ion Torrect A adapter gRNA-6 homology region | GAGUCGGAGACACGCAGGGA |
| 23 | Ion Torrect P adapter gRNA-1 homology region | ACUGCCCAUAGAGAGGAAAG |
| 24 | Ion Torrect P adapter gRNA-2 homology region | AUCACCGACUGCCCAUAGAG |
| 25 | Ion Torrect P adapter gRNA-3 homology region | GCCCAUAGAGAGGAAAGCGG |
| 26 | Ion Torrect P adapter gRNA-4 homology region | GCCUCCGCUUUCCUCUCUAU |
| 27 | ILLUMINA i5 adapter sequence-Distal | AATGATACGGCGACCACCGAGATCTACAC |
| 28 | ILLUMINA i5 adapter sequence-Proximal | ACACTCTTTCCCTACACGACGCTCTTCCGATCT |
| 29 | ILLUMINA i7 adapter sequence-Distal | ATCTCGTATGCCGTCTTCTGCTTG |
| 30 | ILLUMINA i7 adapter sequence-Proximal | AGATCGGAAGAGCACACGTCTGAACTCCAGTCAC |

TABLE 2-continued

Sequences

| SEQ ID NO | Description | Sequence |
|---|---|---|
| 31 | ILLUMINA NEXTERA Read 1 adapter-Distal | AATGATACGGCGACCACCGAGATCTACAC |
| 32 | ILLUMINA NEXTERA Read 1 adapter-Proximal | TCGTCGGCAGCGTCTCAGATGTGTATAAGAGACAG |
| 33 | ILLUMINA NEXTERA Read 2 adapter sequence-Distal | ATCTCGTATGCCGTCTTCTGCTTG |
| 34 | ILLUMINA NEXTERA Read 2 adapter sequence-Proximal | CTGTCTCTTATACACATCTCCGAGCCCACGAGAC |
| 35 | ION TORRENT A Adapter-distal | CCATCTCATCCCTGCGTGTCTCCGACTCAG |
| 36 | ION TORRENT P1 Adapter | ATCACCGACTGCCCATAGAGAGGAAAGCGGAGGCGTAGTGG |
| 37 | Sp_dCas9 | MDKKYSIGLAIGTNSVGWAVITDEYKVPSKKFKVLGNTDRHSIKKNLIGALLFDSGETAEATRLKRTARRRYTRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDVDKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADLFLAAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLLRKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVLPKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVLTLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIANLAGSPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINRLSDYDVDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRMNTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKTEITLANGEIRKRPLIETNGETGEIVWDKGRDFATVRKVLSMPQVNIVKKTEVQTGGFSKESILPKRNSDKLIARKKDWDPKKYGGFDSPTVAYSVLVVAKVEGKSKKLKSVKELLGITIMERSSFEKNPIDFLEAKGYKEVKKDLIIKLPKYSLFELENGRKRMLASAGELQKGNELALPSKYVNFLYLASHYEKLKGSPEDNEQKQLFVEQHKHYLDEIIEQISEFSKRVILADANLDKVLSAYNKHRDKPIREQAENIIHLFTLTNLGAPAAFKYFDTTIDRKRYTSTKEVLDATLIHQSITGLYETRIDLSQLGGD |
| 38 | spCas9 | MDKKYSIGLDIGTNSVGWAVITDDYKVPSKKFKVLGNTDRHSIKKNLIGALLFDSGETAEATRLKRTARRRYTRRKNRICYLQEIFSNEMAKVDDSFFHRLEESFLVEEDKKHERHPIFGNIVDEVAYHEKYPTIYHLRKKLADSTDKADLRLIYLALAHMIKFRGHFLIEGDLNPDNSDVDKLFIQLVQTYNQLFEENPINASRVDAKAILSARLSKSRRLENLIAQLPGEKKNGLFGNLIALSLGLTPNFKSNFDLAEDAKLQLSKDTYDDDLDNLLAQIGDQYADLFLAAKNLSDATLLSDILRVNSEITKAPLSASMIKRYDEHHQDLTLLKALVRQQLPEKYKEIFFDQSKNGYAGYIDGGASQEEFYKFIKPILEKMDGTEELLAKLNREDLLRKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVLPKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVLTLTLFEDKEMIEE |

TABLE 2-continued

Sequences

| SEQ ID NO | Description | Sequence |
|---|---|---|
| | | RLKTYAHLFDDKVMKQLKRRHYTGWGRLSRKLINGIRDKQ SGKTILDFLKSDGFANRNFIQLIHDDSLTFKEAIQKAQVSGQG HSLHEQIANLAGSPAIKKGILQSVKVVDELVKVMGHKPENIV IEMARENQTTQKGQKNSRERMKRIEEGIKELGSQILKEHPVE NTQLQNEKLYLYYLQNGRDMYVDQELDINRLSDYDVDHIVP QSFIKDDSIDNKVLTRSDKNRGKSDDVPSEEVVKKMKNYWR QLLNAKLITQRKFDNLTKAERGGLSELDKAGFIKRQLVETRQ ITKHVAQILDSRMNTKYDENDKLIREVKVITLKSKLVSDFRK DFQFYKVREINNYHHAHDAYLNAVVGTALIKKYPKLESEFV YGDYKVYDVRKMIAKSEQEIGKATAKRFFYSNIMNFFKTEIT LANGEIRKRPLIETNEETGEIVWDKGRDFATVRKVLSMPQVN IVKKTEVQTGALTNESIYARGSFDKLISRKHRFESSKYGGFGS PTVTYSVLVVAKSKVQDGKVKKIKTGKELIGITLLDKLVFEK NPLKFIEDKGYGNVQIDKCIKLPKYSLFEFENGTRRMLASVM ANNNSRGDLQKANEMFLPAKLVTLLYHAHKIESSKELEHEA YILDHYNDLYQLLSYIERFASLYVDVEKNISKVKELFSNIESY SISEICSSVINLLTLTASGAPADFKFLGTTIPRKRYGSPQSILSST LIHQSITGLYETRIDLSQLGSD |
| 39 | Argo-1 Piwi domain-containing protein (WP_058142162.1) | MNNLTFEAFEGIGQLNELNFYKYRLIGKGQIDNVHQAIWSVK YKLQANNFFKPVFVKGEILYSLDELKVIPEFENVEVILDGNIIL SISENTDIYKDVIVFYINNALKNIKDITNYRKYITKNTDEIICKS ILTTNLKYQYMKSEKGFKLQRKFKISPVVFRNGKVILYLNCS SDFSTDKSIYEMLNNGLDVVGLQVKNRWTNSNGNIFIEEVLD KSISEPGTSGKLGQSLIDYYINGNQKYRVEKFTDEDKKAKVI KAKIKNKTYNYIPQALTPVITREYLSHTDKKFSKQIENVIKMD MNYRYQTLKSFVEDIGVIKELNNLHFKNQYYTNFDFMGFES GILEEPVLMGANGKIKDKKQIFINGFFKNPKENVKFGVLYPE GCMENAQSIARSILDFATAGKYNKQENKYISKNLMNIGFKPS ECIFESYKLGDITEYKATARKLKEHEKVGFVIAVIPDMNESEV ENPYNPFKKVWAKLNIPSQMITLKTTEKFKNIVDKSGLYYLH NIALNILGKIGGIPWIIKDMPGNIDCFIGLDVGTREKGIHFPAC SVLFDKYGKLINYYKPTIPQSGEKIAETILQEIFDNVLISYKEE NGEYPKNIVIHRDGFSRENIDWYKEYFDKKGIKFNIIEVKKNI PVKIAKVVGSNICNPIKGSYVLKNDKAFIVTTDIKDGVASPNP LKIEKTYGDVEMKSILEQIYSLSQIHVGSTKSLRLPITTGYAD KICKAIEYIPQGVVDNRLFFL |
| 40 | Argo-2 (EHP50500.1) | MSNLTVEAFEGIGSVNPMLFYQYKVTGKGKYDNVYKIIKSA RYKMHSKNRFKPVFIKDDKLYTLEKLPDIEDLDFANINFVKS EVLSIEDNMSIYGEVVEYYINLKLKKVKVLGKYPKYRINYSK EILSNTLLTRELKDEFKKSNKGFNLKRKFRISPVVNKMGKVIL YLSCSADFSTNKNIYEMLKEGLEVEGLAVKSEWSNISGNLVI ESVLETKISEPTSLGQSLIDYYKNNNQGYRVKDFTDEDLNAN IVNVRGNKKIYMYIPHALKPIITREYLAKNDPEFSKEIEQLIKM NMNYRYETLKSFVNDIGVIEELNNLSFKNKYYEDVKLLGYSS GKIDEPVLMGAKGIIKNKMQIFSNGFYKLPEGKVRFGVLYPK EFDGVSRKAIRAIYDFSKEGKYHGESNKYIAEHLINVEFNPKE CIFEGYELGDITEYKKAALKLNNYNNVDFVIAIVPNMSDEEIE NSYNPFKKIWAELNLPSQMISVKTAEIFANSRDNTALYYLHN IVLGILGKIGGIPWVVKDMKGDVDCFVGLDVGTREKGIHYP ACSVVFDKYGKLINYYKPNIPQNGEKINTEILQEIFDKVLISYE EENGAYPKNIVIHRDGFSREDLDWYENYFGKKNIKFNIIEVK KSTPLKIASINEGNITNPEKGSYILRGNKAYMVTTDIKENLGS PKPLKIEKSYGDIDMLTALSQIYALTQIHVGATKSLRLPITTG YADKICKAIEFIPQGRVDNRLFFL |
| 41 | Argo-3 (1Z25_A Chain A) | SMKAIVVINLVKINKKIIPDKIYVYRLENDPEEELQKEGYSIYR LAYENVGIVIDPENLIIATTKELEYEGEFIPEGEISFSELRNDYQ SKLVLRLLKENGIGEYELSKLLRKFRKPKTFGDYKVIPSVEM SVIKHDEDFYLVIHIIHQIQSMKTLWELVNKDPKELEEFLMTH KENLMLKDIASPLKTVYKPCFEEYTKKPKLDHNQEIVKYWY NYHIERYWNTPEAKLEFYRKFGQVDLKQPAILAKFASKIKKN KNYKIYLLPQLVVPTYNAEQLESDVAKEILEYTKLMPEERKE LLENILAEVDSDIIDKSLSEIEVEKIAQELENKIRVRDDKGNSV PISQLNVQKSQLLLWTNYSRKYPVILPYEVPEKFRKIREIPMFI ILDSGLLADIQNFATNEFRELVKSMYYSLAKKYNSLAKKARS TNEIGLPFLDFRGKEKVITEDLNSDKGIIEVVEQVSSFMKGKE LGLAFIAARNKLSSEKFEEIKRRLFNLNVISQVVNEDTLKNKR DKYDRNRLDLFVRHNLLFQVLSKLGVKYYVLDYRFNYDYII GIDVAPMKRSEGYIGGSAVMFDSQGYIRKIVPIKIGEQRGESV DMNEFFKEMVDKFKEFNIKLDNKKILLLRDGRITNNEEEGLK YISEMFDIEVVTMDVIKNHPVRAFANMKMYFNLGGAIYLIPH KLKQAKGTPIPIKLAKKRIIKNGKVEKQSITRQDVLDIFILTRL NYGSISADMRLPAPVHYAHKFANAIRNEWKIKEEFLAEGFLY FV |

TABLE 2-continued

Sequences

| SEQ ID NO | Description | Sequence |
|---|---|---|
| 42 | Argo-4 (WP_015791216.1) | MKNLRYKINAYRIKKDYIPKEVYRYRIRSFIENINIYRFVGFY GGVALNQSEFILPYPVENLVLEYDGKDVKLEHIDTLNLEDIE NKDKEKAEKLVRGYLTSIYKLKPILYKILRDVRESKIINDIRV DPIPDFTVKRHNNEYYLVIDFNHTATVLKNLWDFVGRDKLK LEDYIGKKIIFKPNPKKRYTIKSIEKQNKKDIDDIVEHIIEYYK WTEEEIKSTFGEIDYTQPIIHCEGIPYPFAPQFCNIVFTMEDLD ENTLKDLQSYWRLPNEIKGNIINQIAKKLRFVENEPIELEFIKF NNTPLIVKDENGKPTKIYTTNRLFRWNYDSKSKLYLPYDIPDI IKNKTLTTFVLIDENLKNVSGKIKRKVYQMFKNYNKIASKTE LPKFDFANKWKYFSNNNIRDVIRKIKDEFNEELGFALIIGNRY YENDYYETLKMQLFNLNIISQNILWENWSKDDNNPMTNNLL IQIMGKLGIKYFALDAKVNYDYIMGLDSGLGAFKSNRVSGC TVIYDSEGKIRRIQPIDVPSPGERIPIHLVVEFLETKTDINMENK NILFLRDGFVQNSEREELKKLSKELNSNIEVISIRKNNKYKVF TSDYGIGSIFGNDGIFLPHKTTFGSNPVKLSTWLRFNSGNEEK LKINESIMQLLYDLTKMNYSALYGEGRNLRIPAPIHYADKFV KALGKNWKIDEELLKHGFLYFI |
| 43 | Argo-5 (NPB03901.1) | MLVNGFKLKIPLIAKDHENRVVEIYSTSTVLKEKFVPYEIPQFI RGREIETWILIDKEIKDNFQEIKKTVIEFFRYYNSIRNNLLPYF KFSYNYVIFSRQNVFKVLTKMNGVDSDAVGFALIIGKQKYR NSDYYEEIKRILFNKNIISQNVLWDQGTLKNNFARNNIIIQILS KLGIKYFVLKYNAEYDYIFGVDIGKEKFSGSSLGGCTIIYDYK GELKKIVPIEILAKKETLNLERIFETLQLDMNLEGKKILLLRDG SIKNFEKEQLKNISKRYHVEITTLNIKKYSKFRIGNDEGGIGVL IEDIALLLPHHYPYGSKPIKIDNKILFKDGNYTELEINANDLEL IYGLSKLNYSSLSSEERILRLPAPVHYAHKFVKALGKGWKIR KDLLEEGCLYFI |
| 44 | Argo-6 (WP_012966655.1) | MMLNIFEVDKNRVEVPQDVYLYKVHLKTLEQRKRDMCIAV LRNSFGYLDVNSFVIYSYKEIRDLPRRIKKYCDLEPTGKVKM NEVDENVRNALVKTFLRSKIRKDIKKLLKKFKKFQQSVGRW TVALDLERIELVEHNGEILVSFNVKLNISSMINLWDIIERDVN RLKGLCWSPENLNDNRIWFRYIPHLIIEEVEDFEESAKSFILSD VHTGEEFGGWTTEDLKKYPENEYGLSEDAIKKIGNYTQFDST QPIIKGVTWSGKEYPFLPQHCIPAYNPMLATAEEKKRIEEIKIN LKNKKDEIIRKIIEQLPYLKQPDNIEIKKVQETARLRAKFVKV EVTKGKITKTLSQPYEKPVSSTLDLFGWISRIIDGGDGIIEICIP DYIPENLSRIKEIEAFLLIENDLNENERKVGDKLLNDAIYVYN FVRSVCLRCGINIPYLNYKGNRFYFENSKEGIRDIYKRITTSLS GEIGFALIFGKRDNYEDEEGEDSFDYYNPLKSALFRNNILSQN FDVTNYVRGDGKINKNTIKYAVSNIIYNIFGKLGVKFFVLEED VPYDYILGIDVGYGEAYTGKVAGCTTVHDSEGRLRNLIPIEK QNYPSKETARIKALLEEIEQKKKIYNIDFENKSILILRDGRINK EEINQLMEFSEERNCRITYIEIRKNIVHQFLVNSSQACYVKIGD YYILKAHNPRIGFPRAIKIARKIVIEGDAWRESSLTEDDILLIY KLTALNYSTIGRDSNLRIPAPIYYADKLVKALKKGWKFDERF LRYGILYFL |
| 45 | Argo-7 (HIP43457.1) | MKGRNNSSLKLNIFRVNLEQLSIPEKIYVYNISANILDSSKLTS FYKRLENIYGFMDTQNRKLYSYKEIDFISKNMKENLNLKLEK TIKLSELESSFRNQILKTYIRNSVKMDINRIIKEIQHQFLGKEK KRTGRWNLSIIPERINVEHINDAFYVAFNVKLRILANKNLWD FIGRDLEKLKTLCWFPDKSKDIKIWFRYVPDLKEENERSYLL TYIQSKDEAKNSGFSFEDLKYYPQEKRNTTYGELKEIAKFED FDENQPIIVGVSSTDMRNPLYFLPQYCIPAYNPVLASENESKK IQKVYESVLFRNKYEIIYKIYDKIPYLELNYEDISFKELDNHRK GKLKVNFVKAKLYLGKDKKDKQGEIIKCKVVGKPQKRTIE NTADLFSWIHKLEDLRGKKKKELIVDIPIPEYVPEYLQKLDEI GTFLLVESGNPSSDIDMIKNFLLLIADVYRVIREASEGFNKIPR LKFIKNPETNRFEFLFKKSSEGIDKTVRELGQLLKKGKKELSE KELGFAFIFGSQDDFVEEHEDFDYYIPLKRNLFLNNILSQNFLI DTYTNKNKIKFALSNIVYNLFGKLGIKFFALEEKVYYDYILGI DTGLAEAYTGRVAGCTTVHDSNGRLKNIIPIEKLNPARRETV RIKALLEEIHIDADYNMDFSNKKILILRDGKIQPEELKQLVEFT KSKKCKITMIDVRKHTVYQWLEKGNDKHLSIKVGDFCLLKP HSPRRGYPRMLKISQKVEIDENGFTYKDLTDYDILLIYKLTLL NYSTIGRPSNLKLPGIYYADKLVKALKRGWKLEPKFLKEGF LYFL |

TABLE 2-continued

Sequences

| SEQ ID NO | Description | Sequence |
|---|---|---|
| 46 | Exemplarily sgRNA of Yin et al. 20017 | GGGCGAGGAGCUGUUCACCGGUUUUAGAGCUAGAAAUA GCAAGUUAAAAUAAGGCUAGUCCGUUAUCAACUUGAAA AAGUGGCACCGAGUCGGUGCUUUUU |
| 47 | His Tag | HHHHHH |

Methods of Polynucleotide Library Normalization

In some aspects, this disclosure provides methods of normalizing the concentration of target polynucleotides between two or more samples (e.g., normalizing between two or more polynucleotide libraries).

"Normalizing", "normalization", and similar terms used herein refer to the process of producing a subsequent sample with a desired concentration of target polynucleotides from an initial sample having a different starting concentration of target polynucleotides than the subsequent sample. In some embodiments, "normalization" of two or more samples results in the production of two or more subsequent samples each having a concentration of target polynucleotides that are more similar to each other after performing the normalization methods than before performing the normalization methods. For example, a first sample (e.g., a first polynucleotide library) may comprise 5-fold more target polynucleotide than a second sample (e.g., a second polynucleotide library). In this example, after normalization of the first sample and the second sample, the difference in concentration between the first sample and the second sample would be less than 5-fold (e.g., less than 4-fold, less than 3-fold, or less than 2-fold). In some embodiments, normalization of two or more samples results in the production of two or more subsequent samples each having equimolar (i.e., 1:1) concentrations. In some embodiments, the method of normalization results in differences in target polynucleotide concentration between two or more samples being less than 50% (e.g., less than 40%, less than 30%, less than 25%, less than 20%, less than 15%, less than 10%, less than 5%, or less than 2.5%). In some embodiments, the method of normalization results in differences in target polynucleotide concentration between two or more samples being 5%-40%, 5%-30%, 5%-20%, 5%-10%, 10%-40%, 10%-30%, or 10%-20% in concentration. In some embodiments, the difference in starting target polynucleotide concentration between two or more samples may be 25 relatively small (e.g., less than 5-10%) prior to performing a method of normalization described herein. In such embodiments, the method of normalization may be performed but the two or more samples may not have a detectably more similar concentration after normalization than before normalization.

"Target polynucleotide" or "target polynucleotides" refers to a polynucleotide that comprises nucleic acids encoding an adapter sequence or a static region of an adapter sequence.

In some embodiments, the target polynucleotide comprises a polynucleotide that comprises (1) nucleic acids encoding an adapter sequence or a sequence that has been added to the polynucleotide for the purpose of normalizing using a method described herein (e.g., a Zinc-finger binding domain or a Talen binding domain) and (2) nucleic acids encoding a sequence of interest. In some embodiments, the target polynucleotide comprises nucleic acids encoding an adapter sequence described herein and nucleic acids encoding a sequence of interest. The sequence of interest may be any sequence for which normalization is desired. For example, a sequence of interest may comprise, but is not limited to, DNA, genomic DNA, circulating tumor DNA, RNA, rRNA, mRNA, miRNA, or cDNA. The adapter sequence may be ligated to the 5' end and/or 3' end of the sequence of interest. In some embodiments, the target polynucleotide comprises a first adapter sequence (e.g., a p5 adapter) on the 5' end of the sequence of interest and a second adapter sequence (e.g., a p7 adapter) on the 3' end of target sequence.

A "sample" refers to a composition or solution comprising one or more target polynucleotides. In some embodiments, the sample comprises a plurality of target polynucleotides. A "plurality" refers to two or more. For example, a plurality of target polynucleotide comprises two or more target polynucleotides. In some embodiments, the plurality of target polynucleotides comprises multiple copies of a single target polynucleotide sequence (e.g., at least 10, at least 100, at least 1000, at least 10,000, at least 100,000, or at least 1,000,000, or at least 10,000,000, at least 100,000,000 target polynucleotides). In some embodiments, the plurality of target polynucleotides comprises different target polynucleotide sequences (e.g., at least 10, at least 100, at least 1000, at least 10,000, at least 100,000, or at least 1,000,000, or at least 10,000,000, at least 100,000,000 different target polynucleotides), but at least some of the target polynucleotides (e.g., all of the target polynucleotides) comprise the same adapter sequence. In some embodiments, the sample comprises a target polynucleotide and other molecules (e.g., polynucleotides that are not target polynucleotides and do not comprise an adapter sequence or comprise a different adapter sequence from the one complementary to the guide polynucleotide). In some embodiments, the sample comprises target polynucleotides comprising nucleic acids encoding genomic DNA. In some embodiments, the sample comprises target polynucleotides comprising nucleic acids encoding an RNA. In some embodiments, the sample comprises target polynucleotides comprising nucleic acids encoding a cDNA (e.g., of mRNA or lncRNA). In some embodiments, the sample comprises target polynucleotides comprising nucleic acids encoding an exon. In some embodiments, the sample comprises target polynucleotides comprising nucleic acids encoding an intron.

In some embodiments, the plurality of target polynucleotides in the sample is present at a concentration of 50 femtomoles (fmols) to 3,400 fmols. In some embodiments, the plurality of target polynucleotides is present at a concentration of 200 fmols to 3,400 fmols. In some embodiments, the plurality of target polynucleotides is present at a concentration of 300 fmols to 3,400 fmols. In some embodiments, the plurality of target polynucleotides is present at a concentration of 500 fmols to 3,400 fmols. In some embodiments, the plurality of target polynucleotides is present at a concentration of 750 fmols to 3,400 fmols. In some embodiments, the plurality of target polynucleotides is present at a concentration of 1,000 fmols to 3,400 fmols. In some embodiments, the plurality of target polynucleotides is present at a concentration of 1,000 fmols to 3,400 fmols. In some embodiments, the plurality of target polynucleotides is present at a concentration of 2,000 fmols to 3,400 fmols. In some embodiments, the plurality of target polynucleotides is present at a concentration of 50 fmols. In some embodiments, the plurality of target polynucleotides is present at a concentration of 3,400 fmols. In some embodiments, the plurality of target polynucleotides is present at a concentration of 500 fmols to 3,400 fmols.

In some embodiments, the method of normalizing is performed for at least 2 samples (e.g., at least 3 samples, at least 4 samples, at least 5 samples, at least 6 samples, at least 7 samples, at least 8 samples, at least 9 samples, at least 10 samples, at least 25 samples, at least 50 samples, at least 75 samples, at least 100 samples, at least 150 samples, or at least 200 samples, at least 300 samples, at least 384 samples, at least 400 samples, at least 500 samples, at least 600 samples, at least 700 samples, at least 800 samples, at least 900 samples, at least 1000 samples, at least 1500 samples, at least 2000 samples, at least 3000 samples, or at least 5000 samples or more). In some embodiments, the method of normalizing is performed for 2-384 samples. In some embodiments, the method of normalizing is performed for 24-384 samples. In some embodiments, the method of normalizing is performed for 24-500 samples. In some embodiments, the method of normalizing is performed for 24-750 samples. In some embodiments, the method of normalizing is performed for 24-1000 samples. In some embodiments, the method of normalizing is performed for 24-2000 samples. In some embodiments, the method of normalizing is performed for 24-3000 samples.

In some embodiments, the samples comprise target polynucleotides at a pre-normalization concentration of within a 70-fold concentration of each other. In some embodiments, the samples comprise target polynucleotides at a pre-normalization concentration of within a 60-fold concentration of each other. In some embodiments, the samples comprise target polynucleotides at a pre-normalization concentration of within a 50-fold concentration of each other. In some embodiments, the samples comprise target polynucleotides at a pre-normalization concentration of within a 40-fold concentration of each other. In some embodiments, the samples comprise target polynucleotides at a pre-normalization concentration of within a 30-fold concentration of each other. In some embodiments, the samples comprise target polynucleotides at a pre-normalization concentration of within a 20-fold concentration of each other. In some embodiments, the samples comprise target polynucleotides at a pre-normalization concentration of within a 10-fold concentration of each other. In some embodiments, the samples comprise target polynucleotides at a pre-normalization concentration of within a 5-fold concentration of each other. In some embodiments, the samples comprise target polynucleotides at a pre-normalization concentration of within a 2-fold concentration of each other. In some embodiments, the samples comprise target polynucleotides at a pre-normalization concentration of within a 1.5-fold concentration of each other.

In some embodiments, this disclosure provides a method for normalizing the concentration of target polynucleotides between at least two samples (e.g., two polynucleotide libraries) each comprising a target polynucleotide, the method comprising, for each sample of the at least two samples: (i) obtaining the sample, wherein the target polynucleotides of the sample comprise an adapter sequence; (ii) producing a solution, the producing comprising combining (a) the sample, (b) a predetermined concentration of a guide polynucleotide comprising a targeting region that is complementary to a static region of the adapter sequence of the target polynucleotides of the sample, and (c) a predetermined concentration of a dCas or a dArgonaute; (iii) contacting the solution with a solid phase comprising a dCas or a dArgonaute binding molecule; (iv) separating the solution from the solid phase; and (v) extracting the target polynucleotides from the solid phase to normalize the concentration of target polynucleotides between the two or more samples.

In some embodiments, this disclosure provides a method for normalizing the concentration of target polynucleotides between at least two samples (e.g., two polynucleotide libraries) each comprising a target polynucleotide, the method comprising, for each sample of the at least two samples: (i) obtaining the sample, wherein the target polynucleotides of the sample comprise an adapter sequence; (ii) producing a solution, the producing comprising combining (a) the sample, (b) a predetermined concentration of a guide polynucleotide comprising a targeting region that is complementary to the adapter sequence of the target polynucleotides of the sample, and (c) a predetermined concentration of a dCas or a dArgonaute; (iii) contacting the solution with a solid phase comprising a dCas or a dArgonaute binding molecule; (iv) separating the solution from the solid phase; and (v) extracting the target polynucleotides from the solid phase to normalize the concentration of target polynucleotides between the two or more samples.

In some embodiments, a method for normalizing the concentration of target polynucleotides between at least two samples comprises a step of obtaining a sample comprising target polynucleotides. The sample may be obtained from any suitable source, including, but not limited to cells (e.g., eukaryotic or prokaryotic cells), tissues (e.g., brain, heart, lung, liver, kidney, adipose, skin, gall bladder, or breast), diseased tissues (e.g., tumor), bodily fluid (e.g., saliva, sweat, blood, urine, mucus, or cerebral spinal fluid), or from in vitro production. In some embodiments, obtaining a sample comprises obtaining polynucleotides of interest (e.g., extracting the polynucleotide of interest from a biological sample) and modifying the polynucleotides of interest to comprise adaptors sequences (e.g., modifying the polynucleotides of interest to become target polynucleotides). Modifying the polynucleotides of interest to comprise adaptor sequences may be performed using any suitable methods, including, but not limited to using a kit for attaching adapter sequences to polynucleotides described herein. In some embodiments, the sample comprises 1-100 nM of target polynucleotides. In some embodiments, the sample comprises 1-1000 nM of target polynucleotides.

In some embodiments, producing a solution, in the context of the method of normalization, refers to combining, the sample and the predetermined concentration of a guide polynucleotide and the predetermined concentration of a dCas or a dArgonaute in an aqueous solution (e.g., a buffer suitable for the method). In some embodiments, producing the solution comprises combining a pre-determined amount of dCas protein or dArgonaute protein and a predetermined amount of guide polynucleotide prior to combining with the sample. In some embodiments, producing a solution comprises combining a predetermined amount of a guide RNA polynucleotide that is RNA with a predetermined amount of dCas9 protein or dArgonaute protein. In some embodiments, producing a solution comprises combining a predetermined amount of a guide polynucleotide that is DNA with a predetermined amount of dArgonaute protein. In some embodiments, producing a solution comprises combining a predetermined amount of a guide RNA comprising a homology region of any one of SEQ ID NOs: 1-26 with a predetermined amount of dCas9 of SEQ ID NO: 37.

A "predetermined concentration" refers to a concentration (e.g., nanomolar) or amount (e.g., nanomoles) of a reagent (e.g., a guide polynucleotide, a dCas protein or a dArgonaute protein) that has been selected for extracting a particular or consistent amount of target polynucleotides from a sample. In some embodiments, the same or similar amounts of a pre-determined concentration of a dCas protein or a dArgonaute protein is added to each sample that is to be normalized. In some embodiments, the same or similar amounts of a pre-determined concentration of a guide RNA polynucleotide is added to each sample that is to be normalized. In some embodiments, a predetermined concentration of a dCas protein or a dArgonaute protein is added to the sample, and a predetermined amount of guide RNA polynucleotide added to the sample is in excess of the predetermined amount of dCas protein or a dArgonaute protein added to the sample. In some embodiments, the predetermined amount of dCas protein or dArgonaute protein is 1-2000 femtomoles. In some embodiments, the predetermined amount of dCas protein or dArgonaute protein is 60-2000 femtomoles. In some embodiments, the predetermined amount of dCas protein or dArgonaute protein is 60-1000 femtomoles. In some embodiments, the predetermined amount of dCas protein or dArgonaute protein is 125-1000 femtomoles. In some embodiments, the predetermined amount of dCas protein or dArgonaute protein is at least 60 femtomoles (e.g., at least 60 femtomoles, at least 125 femtomoles, at least 250 femtomoles, at least 500 femtomoles, at least 750 femtomoles, or at least 1000 femtomoles). In some embodiments, the predetermined amount of dCas protein or dArgonaute protein is 50, 60, 125, 250, 750, 1000, 1500, or 2000 femtomoles. In some embodiments, the predetermined concentration of guide RNA polynucleotides is in excess to the predetermined concentration of dCas9 protein or dArgonaute protein.

In some embodiments, ribonucleoprotein (RNP) complex (e.g., the guide RNA, dCas protein or dArgonaute protein, and adapter sequence) is present at in the sample at a concentration of 250 femtomoles (fmols) to 14,000 fmols. In some embodiments, the RNP complex is present in the sample at a concentration of 300 fmols to 14,000 fmols. In some embodiments, the RNP complex is present in the sample at a concentration of 2,000 fmols to 14,000 fmols. In some embodiments, RNP complex is present in the sample at a concentration of 6,000 fmols to 14,000 fmols. In some embodiments, RNP complex is present in the sample at a concentration of 10,000 fmols to 14,000 fmols. In some embodiments, the RNP complex is present in the sample at a concentration of at least 250 fmols. In some embodiments, RNP complex is present in the sample at a concentration of at least 300 fmols. In some embodiments, the RNP complex is present in the sample at a concentration of at least 2,000 fmols. In some embodiments, RNP complex is present in the sample at a concentration of at least 6,000 fmols. In some embodiments, the RNP complex is present in the sample at a concentration of at least 10,000 fmols. In some embodiments, the RNP complex is present in the sample at a concentration of 250 fmols. In some embodiments, the RNP complex is present in the sample at a concentration of 300 fmols. In some embodiments, the RNP complex is present in the sample at a concentration of 2,000 fmols. In some embodiments, the RNP complex is present in the sample at a concentration of 6,000 fmols. In some embodiments, the RNP complex is present in the sample at a concentration of 10,000 fmols. In some embodiments, the RNP complex is present in the sample at a concentration of 14,000 fmols.

In some embodiments, the method comprising producing a solution comprising a predetermined concentration of a dCas protein comprising an affinity tag or dArgonaute protein comprising an affinity tag as described herein.

In some embodiments, the affinity tag binding molecule comprises a metal ion (e.g., Ni2+) and the affinity tag comprises a His Tag. In some embodiments, the affinity tag binding molecule comprises biotin and the affinity tag comprises avidin. In some embodiments, the affinity tag binding molecule comprises an anti-myc antibody and the affinity tag comprises a myc tag. In some embodiments, the affinity tag binding molecule and a corresponding affinity tag is selected from Table 1.

In some embodiments, the dArgonaute or dCas of the method does not comprise an affinity tag. In some embodiments, the method comprises contacting the solution with a solid phase comprising a molecule that binds to the dCas or the dArgonaute (e.g., an antibody that binds to the dCas or dArgonaute).

In some aspects, the method comprises contacting the solution and a solid phase. In some embodiments, the solid phase comprises a molecule that binds to dArgonaute or dCas (e.g., an antibody or an affinity tag binding molecule). In some embodiments, the solid phase comprises a beads (e.g., a microparticle or a nanoparticle). In some embodiments, the bead is a metal bead, a polymer bead, a protein bead, or a lipid bead. In some embodiments, the bead (e.g., metal bead) comprises metal ions (e.g., Ni2+, Co2+, Cu2+, and/or Zn2+ions) on the surface of the bead. In some embodiments, the metal bead is magnetic (e.g., paramagnetic, diamagnetic, or ferromagnetic).

In some embodiments, the method comprises incubating the solid phase and the solution.

In some embodiments, the incubation is at room temperature. In some embodiments, the incubation is at 30-40 °C. In some embodiments, the incubation is at 35-38 °C. In some embodiments, the incubation is at or about 37 °C. In some embodiments, the incubation is at least 15 minutes (e.g., at least 30 minutes, at least 45 minutes, at least 60 minutes, or at least 2 hours). In some embodiments, the incubation is at least 60 minutes. In some embodiments, the incubation is 15 minutes to 2 hours.

In some embodiments, the method further comprises separating the solution from the solid phase. "Separating" as used in the context of this method, refers to removing the solution from the solid phase or removing the solid phase from the solution. In some embodiments, separating is not a perfect separation, e.g., there may small amount of solution (e.g., less than about 1 microliter of solution) and solid phase that are still in contact with one another after separation. In some embodiments, the purpose of the separating step is to separate the unbound target polynucleotide of the solution from the target polynucleotides bound to the solid phase, which is part of normalizing concentration. This may be done by (1) capturing the magnetic beads bound to target polynucleotides (e.g., using a magnet) (2) removing the solution from the solid phase (e.g., using a pipette) and (3) repeatedly rinsing the solid phase with a buffer (e.g., a buffer that does not denature the Cas protein or the Argonaute protein). In some embodiments, the method comprises washing the solid phase at least 1 (e.g., at least 2, at least 3, at least 4, or at least 5, or more times).

In some embodiments, the method further comprises extracting the target polynucleotide from the solid phase. In some embodiments, the extracting comprising contacting the solid phase with a protease, which proteolyzes the Cas protein or Argonaute protein releasing the target polynucleotides. The protease may be any suitable protease, including, but not limited to trypsin, chymotrypsin, endoproteinase Lys-C, endoprotease AspN, endoprotease GluC, elastase, proteinase K, or papain. Corresponding protease reaction conditions and incubation times are known in the art. In some embodiments, the extracting comprising contacting the solid phase with a protein denaturing agent (e.g., a detergent, and organic solvent, or a chaotropic agent). In some embodiments, extracting comprising increasing the temperature of the solid phase (e.g., by warming a liquid in which the solid phase is located) to denature the Cas protein or Argonaute protein). In some embodiments, extracting comprises increasing or decreasing the pH of liquid in which the solid phase is located.

In some embodiments, the method of normalizing comprises, performing, in sequential order: (i) obtaining the sample, wherein the target polynucleotides of the sample comprise an adapter sequence; (ii) producing a solution, the producing comprising combining (a) the sample, (b) a predetermined concentration of a guide polynucleotide comprising a targeting region that is complementary to the adapter sequence of the target polynucleotides of the sample, and (c) a predetermined concentration of a dCas or a dArgonaute comprising an affinity tag, wherein the predetermined concentration of the dCas or the dArgonaute corresponds to the guide polynucleotide; (iii) contacting the solution with a solid phase comprising an affinity tag binding molecule that is capable of binding to the affinity tag; (iv) separating the solution from the solid phase; and (v) extracting the target polynucleotides from the solid phase to normalize the concentration of target polynucleotides between the two or more samples.

In some embodiments, a method for normalizing the concentration of target polynucleotides between at least two samples comprises, for each sample of the at least two samples: (i) obtaining the sample, wherein target polynucleotides of the sample comprise an adapter sequence of any one of SEQ ID NOs 27-36; (ii) producing a solution, the producing comprising combining (a) the sample, (b) a predetermined concentration of a Cas gRNA polynucleotide comprising a homology region that is complementary to the adapter sequence, and (c) a predetermined concentration of a dCas9 comprises a His-Tag of SEQ ID NO: 47 (e.g., a his-tag on the n-terminus of the dCas9); (iii) contacting the solution with a magnetic solid phase comprising an Ni 2+ ion; (iv) separating the solution from the solid phase; and (v) extracting the target polynucleotides from the solid phase to normalize the concentration of target polynucleotides between the two or more samples.

In some embodiments, a method for normalizing the concentration of target polynucleotides between at least two samples comprises, for each sample of the at least two samples: (i) obtaining the sample, wherein target polynucleotides of the sample comprise an adapter sequence of any one of SEQ ID NOs: 27-36; (ii) producing a solution, the producing comprising combining (a) the sample, (b) a predetermined concentration of a Argonaute guide polynucleotide (e.g., an siDNA) comprising a targeting region that is complementary to the adapter sequence, and (c) a predetermined concentration of a an Argonaute protein comprising a His-Tag of SEQ ID NO: 47; (iii) contacting the solution with a magnetic solid phase comprising an Ni 2+ ion; (iv) separating the solution from the solid phase; and (v) extracting the target polynucleotides from the solid phase to normalize the concentration of target polynucleotides between the two or more samples.

In some aspects, this disclosure provides a method for normalizing the concentration of target polynucleotides between at least two samples each comprising target polynucleotides, wherein the target polynucleotides that are not captured during normalization are digested. In some embodiments, the method comprises, for each sample of the at least two samples: (i) obtaining the sample (e.g., as described herein), wherein the target polynucleotides of the sample comprise an adapter sequence; (ii) producing a solution, the producing comprising combining (a) the sample, (b) a predetermined concentration of a guide polynucleotide comprising a targeting region that is complementary to the adapter sequence of the target polynucleotides of the sample, and (c) a predetermined concentration of a dCas or a dArgonaute comprising an affinity tag; and (iii) contacting the solution with a nuclease (e.g., a catalytically active Cas or Argonaute protein 9) to normalize the concentration of target polynucleotides between the two or more samples (e.g., digest the target polynucleotides that are not bound to the solid phase).

In some embodiments, the method comprises contacting the solution with a nuclease. In some embodiments, the nuclease is an exonuclease. In certain embodiments, the exonuclease is an exonuclease I, exonuclease II, exonuclease III, exonuclease IV, exonuclease V, exonuclease VI, exonuclease VII, or exonuclease VIII. In some embodiments, the nuclease is a catalytically-active Cas RNP or Argonaute RNP. In some embodiments, the catalytically-active Cas RNP or Argonaute RNP comprises a guide polynucleotide that is complementary to an adapter sequence. In some embodiments, the Cas endonuclease is a Cas9 endonuclease. In some embodiments, the Cas endonuclease is a Cpf1, C2c1, C2c3, C2c2, CasX, or CasY endonuclease. In some embodiments, the catalytically-active is an Argonaute protein (e.g., an Argonaute endonuclease). In some embodiments, the Argonaute protein is a CbAgo endonuclease. In certain embodiments, the Argonaute protein is a LrAgo, PfAgo, TtAgo, AaAgo, AfAgo, MjAgo, MpAgo, NgAgo, RsAgo, CpAgo, IbAgo, KmAgo, or SeAgo endonuclease.

In some aspects, the two more samples being normalized (e.g., using the methods described herein) comprise target polynucleotides comprising a first adapter sequence and a second adapter sequence. In some embodiments, the guide polynucleotide targeting region is complementary to the first adapter sequence. In some embodiments, the method further comprises contacting the sample with a primer encoding a nucleic acid sequence that is complementary to a portion of the second adapter sequence and a polymerase (e.g., a DNA polymerase) in conditions sufficient for primer elongation. As described in the "Kits" section, this primer may be used to elongate a target polynucleotide such that first adapter sequence comprises a double stranded PAM for Cas (e.g., dCas) binding. In some embodiments, the primer is complementary to the proximal portion of an adapter sequence (e.g., the second adapter sequence). In such embodiments, elongating the primer to produce a double stranded polynucleotide may not produce an elongated strand that is capable of being sequenced by next-generation sequence because the elongated strand does not comprise the distal portion of the second adapter sequence. This may be advantageous because elongation (e.g., DNA amplification), can introduce artifacts (e.g., mutations) into polynucleotides that may bias or distort sequencing results.

In some embodiments, the primer comprises a nucleic acid sequence that is complementary to any one of SEQ ID NOs: 28, 30, 32, and 34. In some embodiments, the second adapter sequence is a 3' adapter sequence. In some embodiments, the second adapter sequence is a 5' adapter sequence.

As used in herein, the singular forms "a," "an," and "the" include plural referents unless the context clearly dictates otherwise. Thus, for example, reference to "an antibody" optionally includes a combination of two or more such molecules, and the like.

The use of any and all examples or exemplary language (e.g., "such as") provided herein, is intended merely to better illustrate the invention and does not pose a limitation on the scope of the invention unless otherwise claimed.

The terms "may," "may be," "can," and "can be," and related terms are intended to convey that the subject matter involved is optional (that is, the subject matter is present in some examples and is not present in other examples), not a reference to a capability of the subject matter or to a probability, unless the context clearly indicates otherwise.

The terms "optional" and "optionally" mean that the subsequently described event, circumstance, or material may or may not occur or be present, and that the description includes instances where the event, circumstance, or material occurs or is present as well as instances where it does not occur or is not present.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

EXAMPLES

Example 1-Library Normalization by Cas9-Guide Mediated Capture of Library Molecules This Example demonstrates that target polynucleotide concentration can be normalized between samples using a predetermined amount of dCas protein and a gRNA that binds to an adapter sequence of the target polynucleotides.

Polynucleotide library (also called a NGS library) normalization before equimolar pooling of multiple different polynucleotide libraries is a challenge in next generation sequencing workflows. While various strategies for normalization exist, these strategies often require additional steps such as qPCR, or special primers or oligo nucleotides, and are often destructive to unused material.

The normalization method described herein includes a sample comprising a target polynucleotide library, the concentration of which is variable and unknown, and results in the reduction of the concentration of this library to a predetermined value. This enables the target polynucleotide concentration of several unknown target polynucleotide libraries to be normalized to more similar molar concentrations and then pooled by volume prior to loading on the sequencer. The general method relies on capturing a known number of library molecules using an adjustable amount of non-cleaving nucleic acid guided nuclease (e.g., a dCas9 or dArgonaute) attached to magnetic beads (FIG. 1). Excess library molecules are removed by pipette removal of unbound material after magnetic bead separation from the initial binding incubation and subsequent buffer washes. After washes, the magnitude beads from each sample are resuspended in the same amount of buffer. Captured DNA can then be obtained by denaturating the non-cleaving nucleic acid guided nuclease. The resulting solutions are then pooled in equal volume with other libraries prepared in the same manner prior to sequencing.

In this Example, a magnetic bead-compatible form of a nucleic acid guided nuclease (NAGN), capable of specifically binding the target determined by the guide nucleic acid (e.g. guide RNA or DNA) but not cleaving the target (e.g. dCas9 D10A/H840A double mutant), was pre-loaded with Cas guide RNAs that are specific to the adapters which are common to the NGS library polynucleotide (e.g. ILLUMINA i5/i7 sequences). Guide RNA Sequences AA (corresponding with SEQ ID NO: 1) and AB (corresponding with SEQ ID NO: 2) were tested and AA showed higher efficiency. In this case the guide RNA sequences target the i5 region of the ILLUMINA Tru-Seq adapter.

```
Guide RNA Sequence AA:
/AltR1/rArG rArUrC rGrGrA rArGrA rGrCrG rUrCrG rUrGrU rGrUrU rUrUrA rGrArG rCrUrA rUrGrC rU/AltR2/

Guide RNA Sequence AB:
/AltR1/rGrA rUrCrG rGrArA rGrArG rCrGrU rCrGrU rGrUrA rGrUrU rUrUrA rGrArG rCrUrA rUrGrC rU/AltR2/
```

Figure 2:
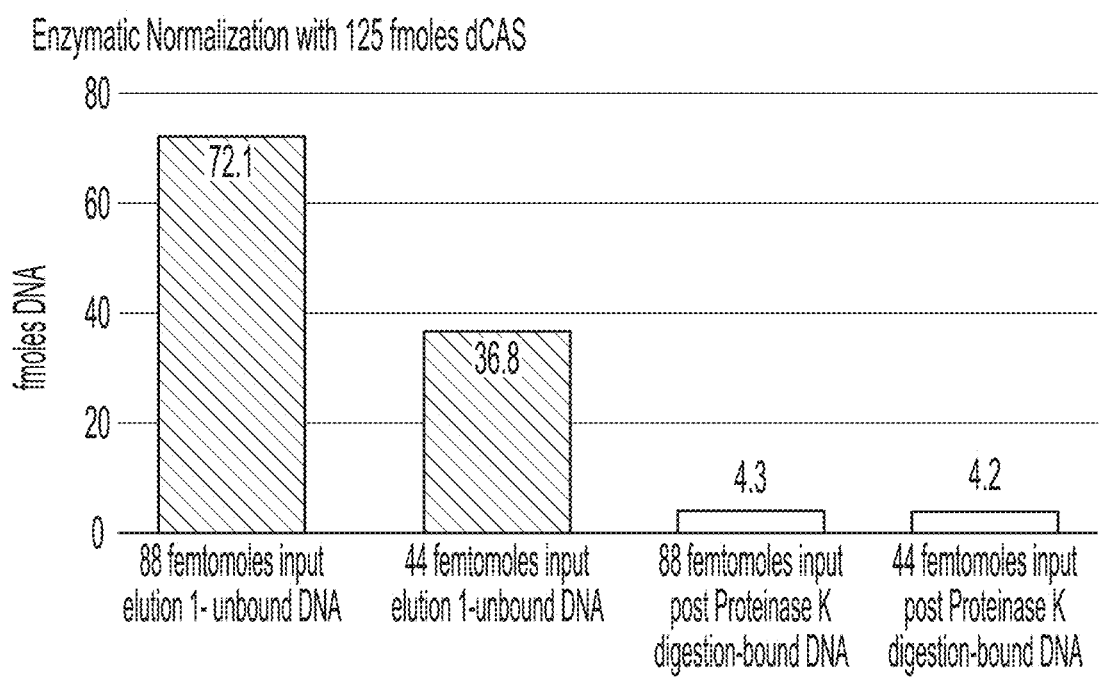
FIG. 2 shows normalization of two different samples each comprising i5-adapter containing polynucleotides. The two different samples of i5-containing DNA fragments were subjected to normalization with the same mass (125 femtomoles, fmols) of dCas9. Following elution after the proteinase digestion, both samples contained an equivalent number of molecules, demonstrating the concept of normalization. The ratio of molecules between the samples changed from 2:1 to 1:1, as intended. If these samples were pooled using equivalent volumes and sequences by NGS, both samples would be expected to yield an equivalent number of clusters.

DNA containing the i5 adapter sequence (target) was normalized using a dCas-Nickel bead pull down system with guide RNA designed to target the i5 adapter sequence. Two samples, a first containing 88 femtomoles of target DNA and second containing 44 femtomoles of target DNA were normalized using with 125 femtomoles of dCas enzyme (FIG. 2). After normalization, the first and second samples were normalized to 4.3 femtomoles and 4.2 femtomoles of target DNA, respectively.

Figure 3:
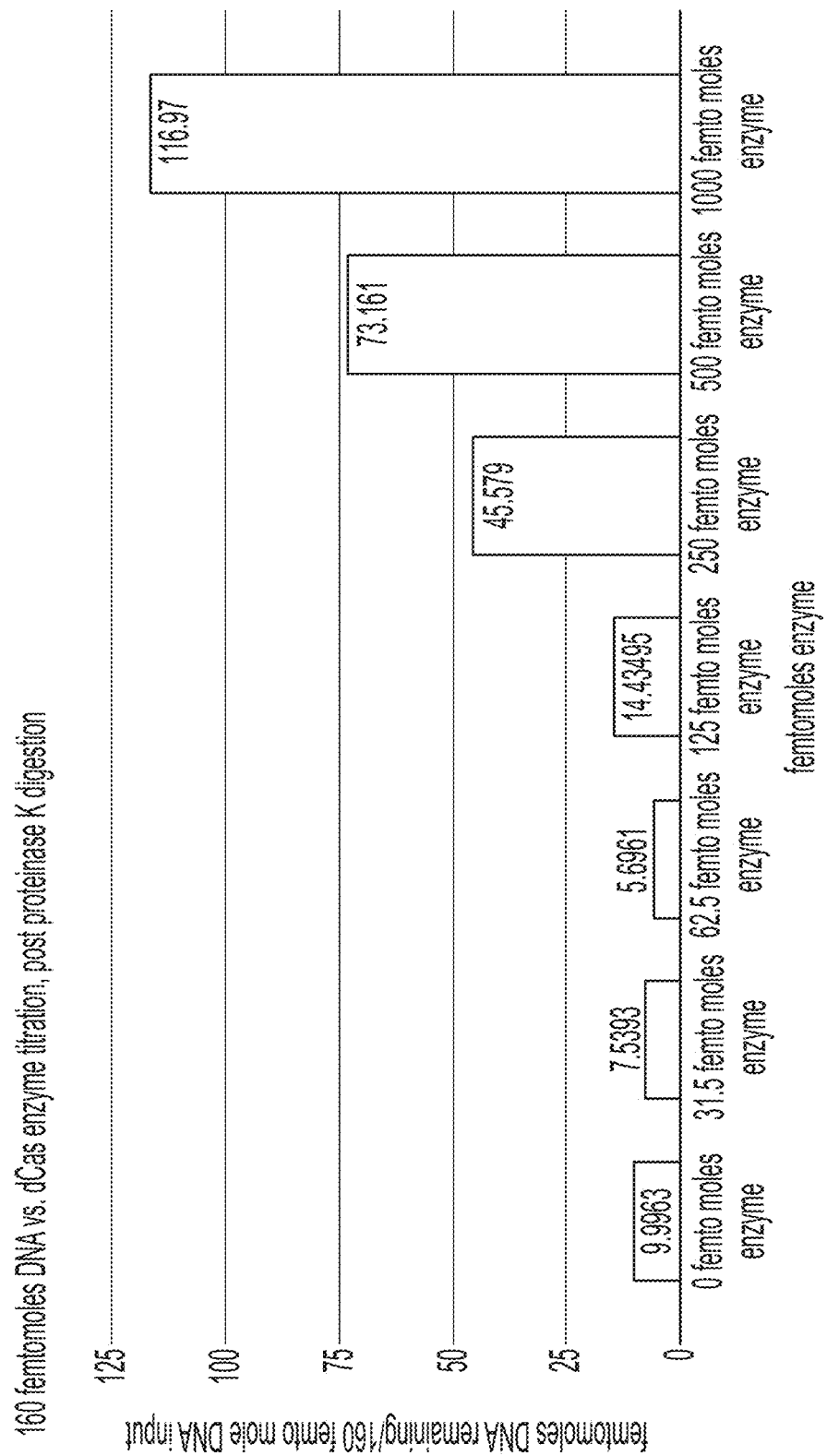
FIG. 3 shows an ability to tune the amount of polynucleotides extracted from a sample by titrating the amount of ribonucleotide protein that binds to the adapters of the polynucleotides (e.g., RNP) being added to the sample. RNP (dCas9-gRNA complex) titration and subsequent bead binding and elution was performed with samples that contained a constant amount of DNA (160 fmols). Increasing the amount of the RNP resulted in linearly increasing amounts of bound (and eventually recovered) DNA. There was a linear relationship in a range from 125 femtomoles to 1000 fmols of RNP at the 160 fmol DNA input level. These data demonstrate that the amount of DNA library extracted can be tuned by adjusting the amount of RNP added to the sample.
Figure 4:
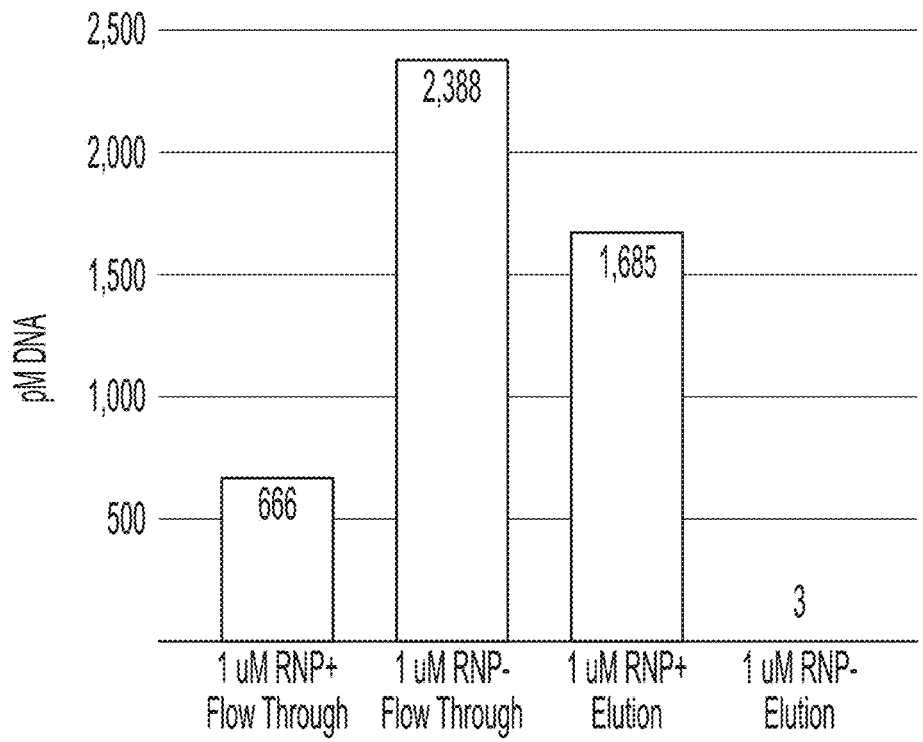
FIG. 4 shows specific and stoichiometric targeting and retention of target DNA molecules driven by interaction with dCas9 RNP and subsequent binding to HisPur beads via the 6His tagged dCas9. A known quantity of i5-sequence containing DNA fragments was bound to HisPur beads after being contacted with RNP (RNP+) or no RNP (RNP-). The majority of the library remained bound to the beads only if exposed to the RNP and eluted after proteinase K digestion (compare RNP+ Flow through to RNP+ elution). In the absence of RNP, all of the DNA was found in the flow through and none bound to the beads (compare RNP– Flow Through to RNP– Elution).
Figure 5:
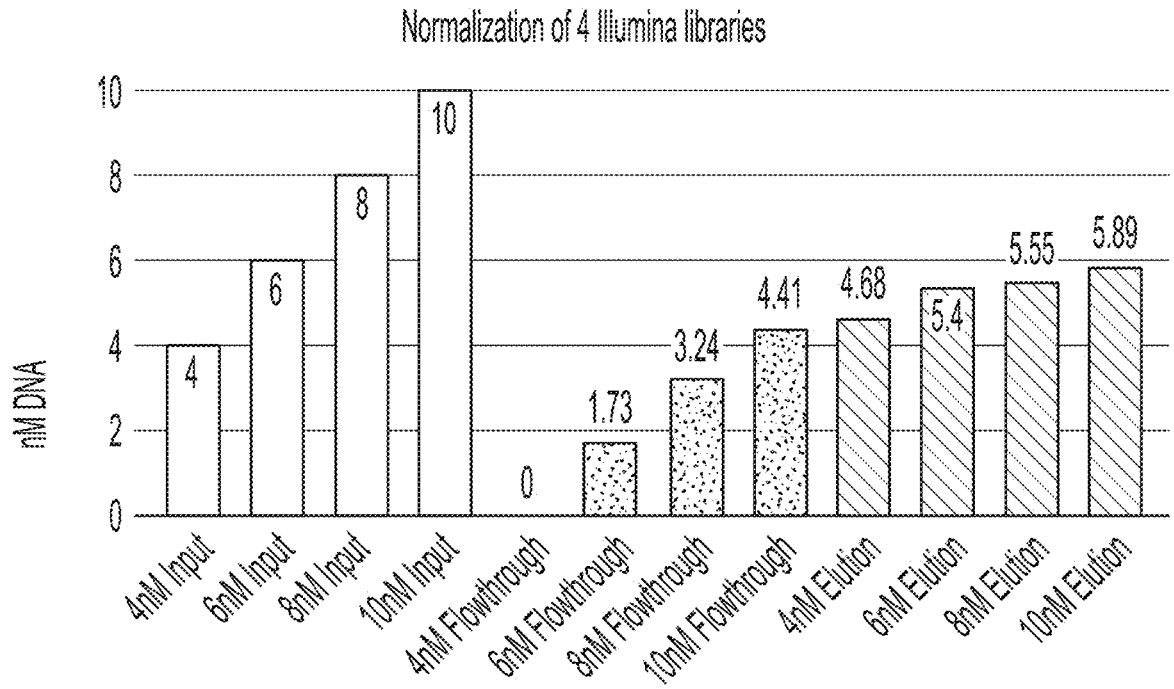
FIG. 5 shows normalization of four different samples of PCR amplified ILLUMINA libraries using dCas9-gRNA complex. Four different samples of PCR amplified ILLUMINA libraries (input), were subjected to normalization with the same mass of dCas9. Following elution after the proteinase digestion (elution), all samples contained a significantly more uniform number of molecules. The highest concentration sample was 25% more concentrated than the lowest, post normalization (4.68 nM Elution vs 5.89 nM Elution), compared to 150% pre-normalization (4 nM Input vs 10 nM Input). In addition, the majority of the unbound library was retained in the flowthrough for all the libraries.
Figure 6:
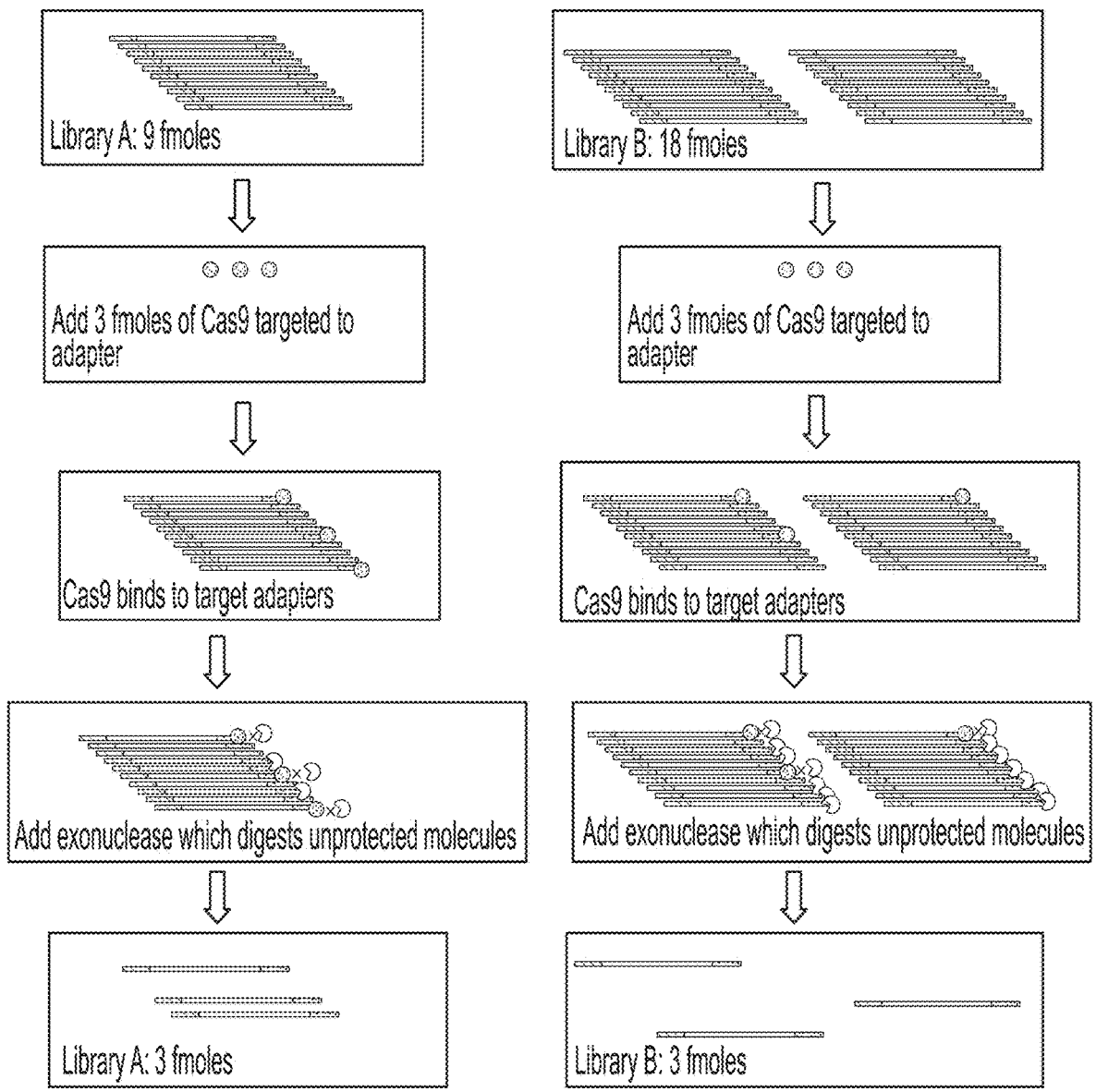
FIG. 6 shows a schematic demonstrating an exemplary embodiment of the disclosed normalization methods. In this exemplary embodiment, two samples are provided that include end-labelled target nucleic acids of different concentrations (Library A having a concentration of 9 fmols and Library B having a concentration of 18 fmols). In this exemplary embodiment, a reaction mixture is produced by adding a predetermined concentration of 3 fmols of a guide polynucleotide and a catalytically-inactive Cas9 protein (which may be pre-assembled) to Library A and Library B and allowing the protein to bind to the adapter sequence at one end of the end-labelled target nucleic acids in the sample, protecting the end of the target nucleic acid from nuclease digestion. An exonuclease is added to the reaction mixture and digests the unprotected nucleic acids. The resulting Library A and Library B each contain 3 fmols of target nucleic acid. In other embodiments, the exonuclease in this schematic may be replaced with a nucleic acid guided nuclease (e.g., Cas9 nuclease), a nucleic acid guided nickase (e.g., Cas9 nickase), a restriction enzyme nuclease or nickase, or a transcription activator-like effector nuclease (TALEN) or another similar nuclease or nickase.

Normalization was further demonstrated by normalizing a dilution series of ILLUMINA DNA sequencing libraries comprising 4 nM, 6 nM, 8 nM and 10 nM of input DNA could be normalized to 4.68 nM, 5.4 nM, 5.55 nM, and 5.89 nM, respectively. (FIG. 5). These results further demonstrate that this method can be used to normalize the concentration of target polynucleotides in samples where the samples have more than a 2-fold difference in starting concentration. Results also showed that the capture of target-containing DNA molecules was driven specifically by the presence of dCas9 RNP (FIG. 4). Additionally, the amount of target DNA extracted per sample using the normalization method could be tuned in a linear manner by increasing the dCas9 RNP (dCas9+Cas gRNA) concentration (FIG. 3). Thus, one may be able to predict the amount of target polynucleotides that will be extracted from sample based on the amount of the dCas9 RNP used.

Methods

1. Form the Ribonucleoprotein (RNP) Binding Complex

Combine 1 uM guide RNA, 1 uM dCas9 enzyme (6His-tagged), and 1X Cas9 dilution buffer and allow the reaction to incubate at room temperature for 5-10 minutes. This creates the RNP specific to the i5 sequence of the library adapter and allows specific targeting of library molecules with precise amounts of dCas9.

2. Perform DNA Binding Reaction.

Combine 10X Cas9 Reaction Buffer, a desired nM of DNA Library, 1 uM RNP complex, and dilute the 10X Cas9 Reaction Buffer to 1x using milliQ water. Incubate the reaction for 1 hr at 37° C. This results in dCas9 bound to library molecules in a tight and specific manner, allowing the subsequent capture using Nickel magnetic beads e.g., His-Pur (Thermo Scientific).

3. Bead Pulldown

To each DNA binding reaction add HisPur magnetic beads and 1X Cas9 reaction buffer and incubate for 15 minutes. Remove supernatant and wash samples twice with 1X Cas Reaction buffer to remove unbound DNA.

4. Proteinase K Digestion (Elution)

Incubate samples with Proteinase K for 10 minutes at 56° C. to release (elute) the bound DNA from the dCas enzyme.

5. Quantification

Flowthrough and final eluted library were quantified using library-specific primers via qPCR.

Step 1.1 PCR-Free Library Normalization by Cas9-Guide Mediated Capture of Library Molecules.

Optionally, this method may include an additional step (step 1.1) for producing a double stranded PAM site on a single stranded target polynucleotide without requiring PCR amplification (FIG. 7A-D). PCR amplification is a popular strategy in the construction of NGS libraries, in particular because it allows for NGS sequencing on small amounts of sample.

However, PCR amplification can be problematic for a number of NGS applications. For example, PCR amplification can introduce GC bias, which interferes with data analysis, such as the identification of novel single-nucleotide polymorphisms (SNPs). To allow library normalization as described in Example 1 while avoiding PCR amplification, the workflow described in this Example introduces a step of library molecule denaturation and partial extension. Step 1.1 is performed before the RNP binding complex is combined with the target nucleotides.

Figure 7A:
FIGS. 7A-D show a schematic of library molecule denaturation and partial sequence extension to produce a double stranded PAM site.
Figure 7B:
Figure 7C:
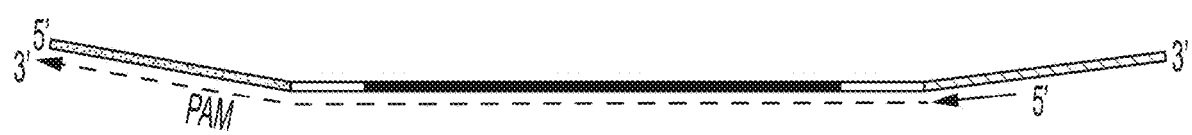
Figure 7C:
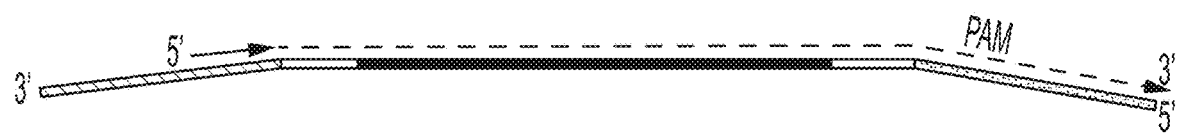
Figure 7D:
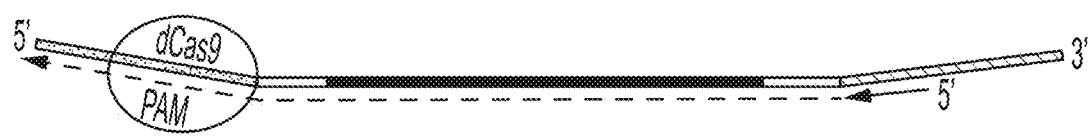
Figure 7D:
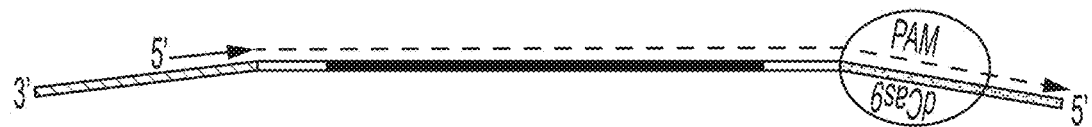

This step begins with a sample having target polynucleotide comprising a 3' and a 5' adapter sequence (FIG. 7A). The reverse complement of the PAM site is encoded on the 5' adapter. A partial primer—which is complementary to a portion of the 3' adapter sequence such that when the partial primer is extended it does produce a reverse complement of the entire 3' adapter sequence—is contacted with the target polynucleotide (FIG. 7B) in conditions such that primer extension can occur (FIG. 7C), e.g., the conditions include the presence of a DNA polymerase. This produces a double stranded PAM site that can be bound an dCas protein used in the normalization method, as described herein (FIG. 7D). However, the elongated primer does not comprise a complete 3' adapter and therefore is not sequenced during next generation sequences. Thus, sequencing results are not biased by amplified DNA (e.g., the elongated primer).

Methods

In order to produce a partial second strand which will enable, for example, an Illumina PCR-free library to be normalized the following approach can be used:

Combine a ligated, unamplified library with an excess of a primer specific to the i7 adapter sequence, for example: 5'GTGACTGGAGTTCAGACGTGT3'(SEQ ID NO: 49). This primer binds to the proximal part of the i7 adapter and crucially does not include the flow cell binding sequences from the distal adapter part. After primer binding, extend the primer using a polymerase in the presence of dNTPs. The resulting extended strand will not be capable of binding to the flow cell and cluster and is thus inert. Following extension, subject the library to the normalization workflows as described in this specification.

Advantages of this Method:

Only the original PCR-free molecules will be capable of clustering.

This method ensures that only fully ligated library molecules (molecules which have a 5' and 3' adapter ligated to the insert) will be targeted by the dCas9 (or other nucleic acid guided nuclease) in the subsequent normalization step.

Detailed Protocol.

1. Combine a 100 femtomoles of ligated library with 500 femtomoles of i7 complement primer (5'GTGACTGGAGTTCAGACGTGT3' (SEQ ID NO: 49)) in the presence of 1X PCR buffer (Tris-HCl pH 8: 20 mM, Magnesium chloride (MgCl2): 2 mM, Potassium chloride (KCl): 50 mM, dNTPs (each): 200 µM together with 1 unit of Taq polymerase.

Any other polymerase can be used here, such as Bst, KOD etc.

2. Subject the sample to a single denaturation-extension step: 95C for 30 s followed by 60C for 1 minute.

3. Optionally, purify the extended duplex using SPRI beads (Ampure XP or equivalent) and subject the extended library to normalization using the methods described in the examples.

4. Only the original ligated library molecule will be capable of clustering on NGS sequencers as it contains both 5' and 3' adapters.

Example 2—Normalizing Samples for NGS with Catalytically-Inactive Cas9 Protein Binding and Exonuclease Digestion A NGS library is provided for which the exact concentration of nucleic acids is unknown but that is at least 20 nM (20 fmol/uL). The nucleic acids in the library have an adapter sequence (e.g., ILLUMINA P5/P7 sequence and a shared Y-adapter sequence (e.g., 13 bp)) on the first and second end of the nucleic acid. The library is combined with a predetermined amount (80 fmol) a catalytically-inactive Cas9 protein having D10A and H840A substitutions. The catalytically-inactive Cas9 protein is preloaded with two different guide RNAs or guide DNAs that are each specific to one of the adapter sequences present on the nucleic acids in the NGS library (e.g., the P5 sequence, the P7 sequence, or the shared Y-adapter sequence). Alternatively, the catalytically-inactive Cas9 protein is preloaded with a single guide RNA or guide DNA that is specific to the Y-adapter sequence present on the nucleic acids in the NGS library or a single guide RNA or guide DNA specific to another sequence that is the same on both ends of the nucleic acids in the NGS library). The reaction mixture is incubated under conditions that promote the specific and strong (guide-directed) association of the catalytically-inactive Cas9 protein with the adapter sequence. This incubation results in a specific number of library molecules (80 fmol) being bound by the catalytically-inactive Cas9 protein at their termini. A non-targeted nuclease, exonuclease III, is added to the reaction mixture under conditions which maintain a specific binding of the catalytically-inactive Cas9 protein with the adapter sequence but that also allow for the non-targeted exonuclease activity. Only the specific number of library molecules (80 fmol) bound by the catalytically-inactive Cas9 protein at their termini remain in the resulting NGS library, with the remaining unprotected molecules partially or fully digested by the nuclease.

These steps are performed simultaneously or sequentially on one or more additional NGS libraries for which the exact concentration of nucleic acids is unknown but that is at least 20 nM (20 fmol/uL). The resulting NGS libraries (which now have concentrations that are more similar between the NGS libraries than the starting concentrations) are pooled, and a purification is performed to remove the catalytically-inactive Cas9 protein from the nucleic acids. The nucleic acids in the libraries are sequenced if at the desired concentration. If the nucleic acids in the library are not yet at the desired concentration, they are amplified and then sequenced.

Example 3—Normalizing Samples for NGS with Catalytically-Inactive CbAgo Protein Binding and Exonuclease Digestion A NGS library is provided for which the exact concentration of nucleic acids is unknown but that is at least 20 nM (20 fmol/uL). The nucleic acids in the library have an adapter sequence (e.g., ILLUMINA P5/P7 sequence and a shared Y-adapter sequence (e.g., 13 bp)) on the first and second end of the nucleic acid. The library is combined with a predetermined amount (80 fmol) of a catalytically-inactive CbAgo protein. The catalytically-inactive CbAgo protein is preloaded with one or more guide DNAs that are specific to the adapter sequence present on the nucleic acids in the NGS library (e.g., the P5 sequence, the P7 sequence, or the shared Y-adapter sequence). The reaction mixture is incubated under conditions that promote the specific and strong (guide-directed) association of the catalytically-inactive CbAgo protein with the adapter sequence. This incubation results in a specific number of library molecules (80 fmol) being bound by the catalytically-inactive CbAgo protein at their termini. A non-targeted nuclease, exonuclease III is added to the reaction mixture under conditions which maintain a tight binding of the catalytically-inactive CbAgo protein with the adapter sequence but that also allow for the non-targeted exonuclease activity. Only the specific number of library molecules (80 fmol) bound by the catalytically-inactive CbAgo protein at their termini remain in the resulting NGS library.

These steps are performed simultaneously or sequentially on one or more additional NGS libraries for which the exact concentration of nucleic acids is unknown but that is at least 20 nM (20 fmol/uL). The resulting NGS libraries (which now have concentrations that are more similar between the NGS libraries than the starting concentrations) are pooled, and a purification is performed to remove the catalytically-inactive CbAgo protein from the nucleic acids. The nucleic acids in the libraries are sequenced if at the desired concentration. If the nucleic acids in the library are not yet at the desired concentration, they are amplified and then sequenced.

Example 4—Alternate Methods for Normalizing Samples for NGS Using Other Nucleases The normalization methods are performed as described in Example 2 or 3, with the exception that the non-targeted nuclease, exonuclease III, is replaced with exonuclease I, a restriction enzyme, or a sequence-specific nuclease. For example, the nuclease is a 5' to 3' exonuclease or a 3' to 5' exonuclease, a single strand-specific nuclease, a double strand-specific nuclease, or a mixture thereof. Alternatively, the non-targeted nuclease is replaced with a catalytically-active nucleic acid guided nuclease (e.g., Cas9, CbAgo). In some embodiments of the methods, the non-targeted nuclease is replaced with a nucleic acid guided nickase (e.g., Cas9 nickase). In certain embodiments, the nucleic acid guided nickase is a Cas9 nickase that has a D10A mutation or an H840A mutation. In some embodiments, the non-targeted nuclease is replaced with a transcription activator-like effector nuclease (TALEN) or TALE nickase. In certain embodiments, the TALEN or TALE nickase targets the same adapter sequence as the nucleic acid binding protein (e.g., dCas protein, dAgo, etc.) used in the method.

Example 5—Normalizing Samples for NGS with Catalytically-Inactive Cas9 Protein Binding and Cas9 Nickase Digestion A NGS library is provided for which the exact concentration of nucleic acids is unknown but that is at least 20 nM (20 fmol/uL). The nucleic acids in the library have an adapter sequence (e.g., ILLUMINA P5/P7 sequence and a shared Y-adapter sequence (e.g., 13 bp)) on the first and second end of the nucleic acid. The library is combined with a predetermined amount (80 fmol) of a nucleic acid guided binding protein to create a reaction mixture. The nucleic acid guided binding protein is a catalytically-inactive Cas9 protein having D10A and H840A substitutions. The catalytically-inactive Cas9 protein is preloaded with a single guide RNA or guide DNA that is specific to the shared Y-adapter sequence present on the nucleic acids in the NGS library. The reaction mixture is incubated under conditions that promote the specific and strong (guide-directed) association of the catalytically-inactive Cas9 protein with the adapter sequence. This incubation results in a specific number of library molecules (80 fmol) being bound by the catalytically-inactive Cas9 protein at their termini. A Cas9 nickase is added to the reaction mixture under conditions which maintain a specific binding of the catalytically-inactive Cas9 protein with the adapter sequence but that also allow for the targeted Cas9 nickase activity. Only the specific number of library molecules (80 fmol) bound by the catalytically-inactive Cas9 protein at their termini remain in the resulting NGS library, with the remaining unprotected molecules partially or fully digested by the Cas9 nickase.

These steps are performed simultaneously or sequentially on one or more additional NGS libraries for which the exact concentration of nucleic acids is unknown but that is at least 20 nM (20 fmol/uL). The resulting NGS libraries (which now have concentrations that are more similar between the NGS libraries than the starting concentrations) are pooled, and a purification is performed to remove the proteins from the nucleic acids. The nucleic acids in the libraries are sequenced if at the desired concentration. If the nucleic acids in the library are not yet at the desired concentration, they may be amplified and then sequenced.

Example 6—Alternate Methods for Normalizing Samples for NGS Including Amplification Before Digestion A NGS library is provided for which the exact concentration of nucleic acids is unknown. The nucleic acids in the library have an adapter sequence (e.g., ILLUMINA P5/P7 sequence and a shared Y-adapter sequence (e.g., 13 bp)) on the first and second end of the nucleic acid. An amplification is performed with primers that bind to the adapter sequence, producing an amplified library.

The amplified library is combined with a predetermined amount (80 fmol) of a nucleic acid guided binding protein to create a reaction mixture. The nucleic acid guided binding protein is a dCas9, a catalytically-inactive Cas9 protein having D10A and H840A substitutions. The catalytically-inactive Cas9 protein is preloaded with a guide RNA or guide DNA that is specific to the adapter sequence present on the nucleic acids in the NGS library (e.g., the P5 sequence, the P7 sequence, or the shared Y-adapter sequence). The reaction mixture is incubated under conditions that promote the specific and strong (guide-directed) association of the catalytically-inactive Cas9 protein with the adapter sequence. This incubation results in a specific number of library molecules being bound by the catalytically-inactive Cas9 protein at their termini. A non-targeted nuclease, exonuclease III, is added to the reaction mixture under conditions which maintain a tight binding of the catalytically-inactive Cas9 protein with the adapter sequence but that also allow for the non-targeted exonuclease activity. Only the specific number of library molecules bound by the catalytically-inactive Cas9 protein at their termini remain in the resulting NGS library.

These steps are performed simultaneously or sequentially on one or more additional NGS libraries. That is, the dCas9 is bound to individual libraries, the protected libraries are pooled, the pool of protected libraries is exposed to an excess of nuclease (e.g., exonuclease III, exonuclease I, restriction enzyme, sequence-specific nuclease, 5' to 3' exonuclease, 3' to 5' exonuclease, single strand-specific nuclease, double strand-specific nuclease, catalytically-active nucleic acid guided nuclease (e.g., Cas9, CbAgo), nucleic acid guided nickase (e.g., Cas9 nickase), transcription activator-like effector nuclease (TALEN), or TALE nickase, or a mixture thereof). The resulting NGS libraries (which now have concentrations that are more similar between the NGS libraries than the starting concentrations) are pooled, and a standard SPRI purification is performed on the pooled NGS libraries. The nucleic acids in the libraries are then sequenced.

Example 7—Normalization of Sequencing Libraries Post Amplification

Figure 8:
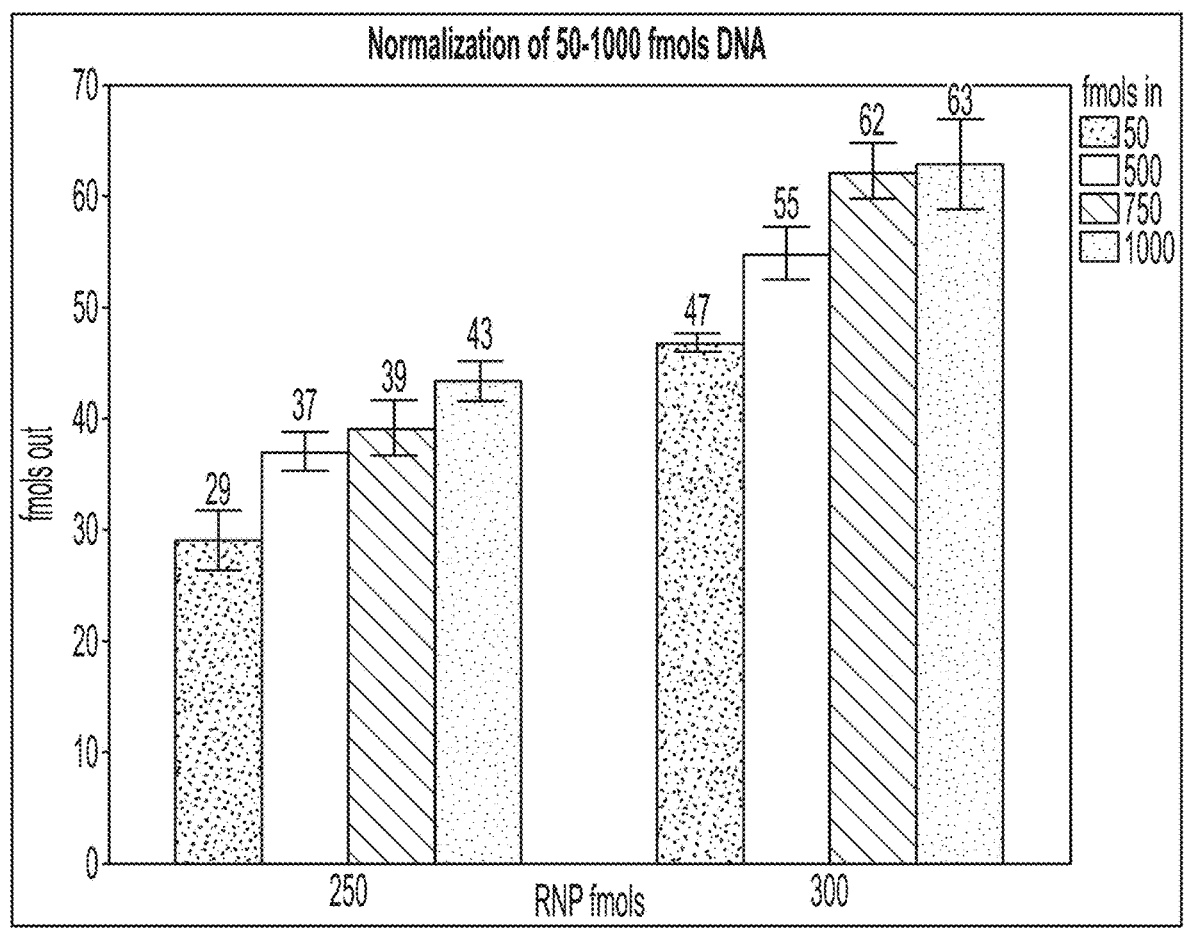
FIG. 8 is a bar graph showing femtomoles of captured DNA (fmols) out) after normalization and amplification for different amounts of starting DNA (fmols in) and two concentrations of ribonucleoprotein (RNP fmols).

Typical Illumina sequencer library preparation chemistries target a final amplified library molar amount between 200 and 1,000 femtomoles (fmols). To demonstrate the capability of library normalization across a range of input, an Illumina TruSeq adapter-ligated double stranded DNA (dsDNA) library was amplified to produce a high concentration DNA input. DNA input amounts of 50, 500, 750, or 1,000 fmols of this DNA was used as input into two different normalization reactions containing either 250 fmols or 300 fmols of ribonucleoprotein (RNP, e.g., dCas9-guide RNA complex). The resulting normalized library was quantified using an HSD1000 DNA tape on an Agilent Tapestation with a region of 100-1,000 base pairs. Both 250 fmols and 300 fmols of RNP normalized the range of DNA library input, with the resulting amount of normalized output being dependent on the RNP amount. Between the low DNA input of 50 fmols and the high DNA input of 1,000 fmols, there was a 20-fold difference in DNA amount. After normalization with 250 fmols of RNP, there was only a 1.5 fold difference, and after normalization with 300 fmols of RNP, there was only a 1.3 fold difference. Between all samples normalized with 250 fmols of RNP, there was an average output of 37 fmols, while a normalization with 300 fmols of RNP resulted in an average output of 56 fmols, demonstrating that the amount of library retained during normalization can be modulated by the amount of RNP used (FIG. 8).

Example 8—Normalization of Sequencing Libraries Pre Targeted Capture

Figure 9:
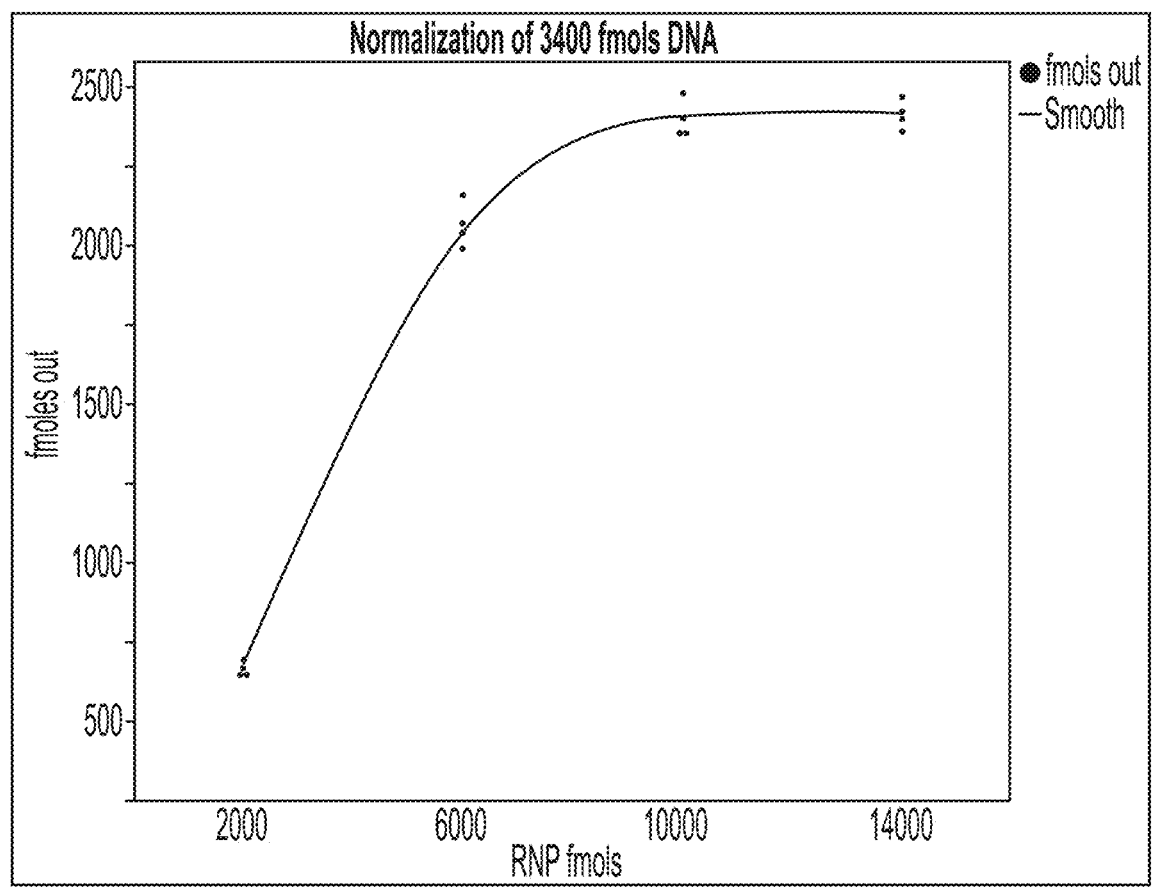
FIG. 9 shows fmols of DNA captured (fmols out) by varying concentrations of ribonucleoprotein (RNP fmols). The concentration of input DNA is shown a 3,400 fmols.

Targeted capture/enrichment panels typically require high masses of amplified library, often ranging from 100ng-1, 000ng of library molecules. Though dependent on library size, such a mass range broadly corresponds to 300-2,000 fmols of DNA. To demonstrate the capabilities of normalization to achieve this final output range, an Illumina TruSeq adapter-ligated dsDNA library was amplified to produce a high concentration of DNA input and 3,400 fmols of this DNA was used as input. Normalization was performed with 2,000, 6,000, 10,000, or 14,000 fmoles of RNP. The output DNA was analyzed using a D1000 tape on an Agilent Tapestation with a region setting of 180-1,000 base pairs. Increasing RNP resulted in the capture of more DNA library. By increasing RNP to 6,000 fmols, about 2,000 fmols of library was captured, supporting normalization for use upstream of target enrichment and similar applications (FIG. 9).

Example 9. Normalization Using a Single Guide RNA (sgRNA) in the RNP

Using a single guide RNA (sgRNA) as opposed to a separate CRISPR RNA (crRNA) and trans-activating CRISPR RNA (tracrRNA) offers a simpler format for performing normalization. To demonstrate similar performance to crRNA/tracrRNA RNPs, an Illumina TruSeq adapter-ligated dsDNA library was amplified to produce a high concentration of DNA input, and 500 fmols of this DNA was used. Normalization was performed with 250, 600, or 1,000 fmols of RNP containing either a crRNA/tracrRNA (duplex guide) or a sgRNA. The sgRNA sequence was:

(SEQ ID NO: 48)
5'-mA*mG*mA* rUrCrG rGrArA rGrArG rCrGrU rCrGrU rGrUrG rUrUrU rUrArG rArGrCrUrArG rArArA rUrArG rCrArA rGrUrU rArArA rArUrA rArGrG rCrUrA rGrUrC rCrGrU rUrArU rCrArA rCrUrU rGrArA rArArA rGrUrG rGrCrA rCrCrG rArGrU rCrGrG rUrGrC mU*mU*mU*rU-3'

(mA/mG/mU are 2'-O-methyl RNA bases;

*indicates phosphorothioate linkages).

The crRNA sequence was:

(SEQ ID NO: 50)
5'-/AltR1/rGrCrA rCrGrG rArGrA rCrGrG rArUrG rUrUrA rUrUrGrUrU rUrArG rArGrC rUrArUrGrCrU/

AltR2/-3' (/AltR1/ and /AltrR2/ are proprietary

IDT modifications).

Figure 10:
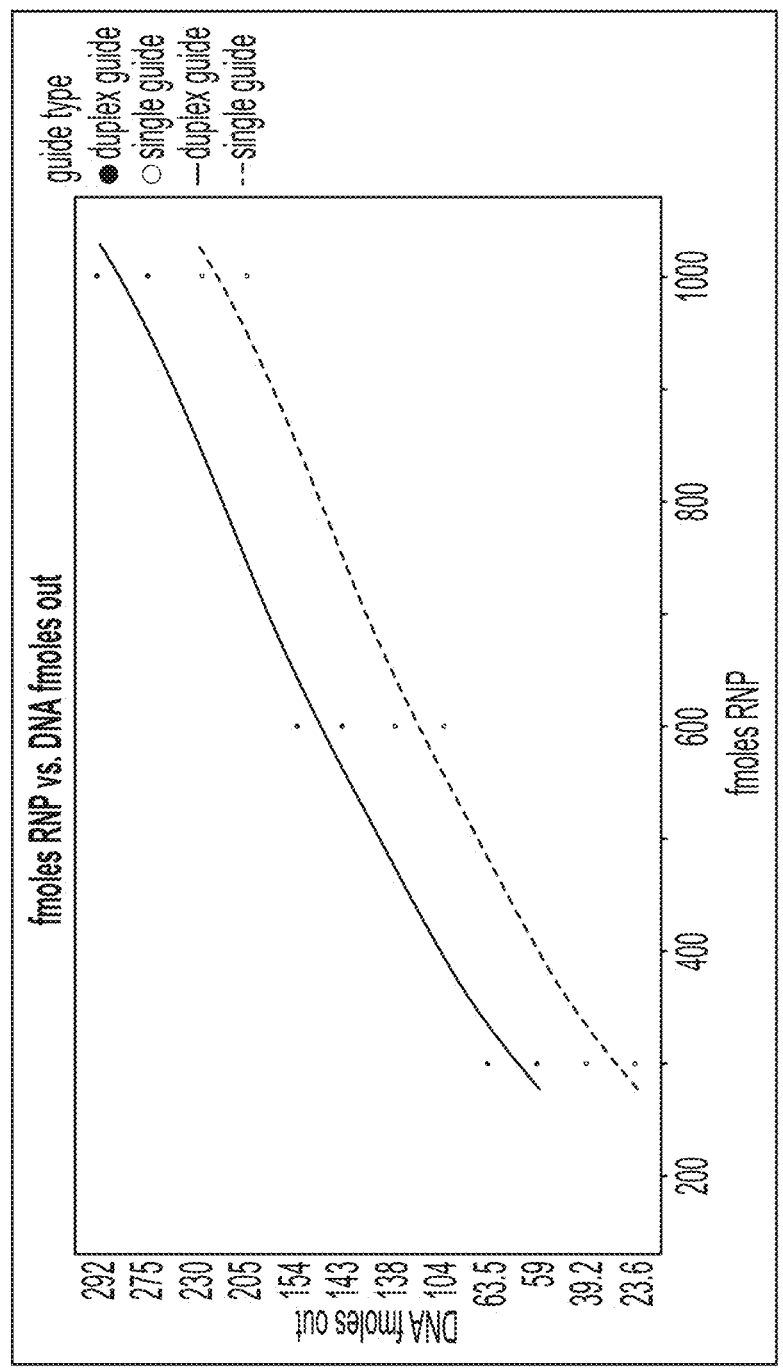
FIG. 10 shows fmols of DNA captured (fmols out) by varying concentrations of ribonucleoprotein (RNP fmols) and either single guide (bottom line) or duplex guide (top line).

The output DNA was analyzed using a D1000 tape on an Agilent Tapestation with a region setting of 180-1,000 base pairs. RNP containing a sgRNA was found to perfor similarly to RNP containing a crRNA/tracrRNA. The sgRNA containing RNPs retained about 20% less DNA than RNPs containing crRNA/tracrRNA. However, increasing fmols of sgRNA RNP resulted in more captured DNA, allowing for ranges demonstrated with crRNA/tracrRNA to be achieved with an sgRNA (FIG. 10).

The examples are provided to illustrate the disclosure but not to limit its scope. Other variations of the disclosure will be readily apparent to one of ordinary skill in the art and are encompassed by the appended claims.

The invention claimed is:

1. A method for normalizing the concentration of target polynucleotides between at least two samples each comprising target polynucleotides, the method comprising, for each sample of the at least two samples:
   (i) obtaining the sample, wherein the target polynucleotides of the sample comprise:
      a first adapter sequence comprising a proximal portion, and a distal portion comprising a sequence that binds to an adapter binding site of a next-generation sequencing platform during next-generation sequencing; and
      a second adapter sequence;
   (ii) contacting the target polynucleotides with primers that are complementary to the proximal portion of the first adapter sequence;
   (iii) extending the primers to produce reverse complements of the target polynucleotides that do not comprise a reverse complement of the distal portion of the first adapter sequence, thereby producing partially double stranded polynucleotides comprising a double stranded second adapter sequence;
   (iv) producing a solution, the producing comprising combining: (a) the partially double stranded polynucleotides, (b) a predetermined concentration of a guide polynucleotide comprising a targeting region that is complementary to a strand of the double stranded second adapter sequence; and (c) a predetermined concentration of a dCas or a dArgonaute comprising an affinity tag, wherein the dCas or the dArgonaute is cognate to the guide polynucleotide;
   (v) contacting the solution with a solid phase comprising an affinity tag binding molecule that is capable of binding to the affinity tag;
   (vi) separating the solution from the solid phase; and
   (vii) extracting the target polynucleotides from the solid phase to normalize the concentration of target polynucleotides between the two or more samples.

2. The method of claim 1, wherein the targeting region is complementary to a static region of the proximal portion.

3. The method of claim 1, wherein the guide polynucleotide comprises a CRISPR-associated protein (Cas) guide RNA (gRNA) polynucleotide or an Argonaute guide polynucleotide.

4. The method of claim 3, wherein the Cas gRNA polynucleotide targeting region is a homology region.

5. The method of claim 4, wherein the Cas gRNA polynucleotide comprises a homology region of any one of SEQ ID NOs: 1-6, 9-19 and 21-26.

6. The method of claim 5, wherein the Cas gRNA polynucleotide comprises a homology region of SEQ ID NO: 1.

7. The method of claim 1, wherein the guide polynucleotide comprises a modified nucleic acid.

8. The method of claim 1, wherein the dCas is a catalytically-inactive Cpf1, C2c1, C2c3, C2c2, CasX, Cas9, or CasY protein.

9. The method of claim 8, wherein the dCas protein comprises an amino acid sequence of SEQ ID NO: 37.

10. The method of claim 1, wherein the affinity tag binding molecule comprises $Ni^{2+}$ and the affinity tag comprises a His Tag.

11. The method of claim 1, wherein extracting the target polynucleotides from the solid phase comprises combining the solid phase and a protease.

12. The method of claim 1, wherein normalizing comprises making the concentration of the of target polynucleotides between the at least two samples within 15% of one another after normalization.

13. The method of claim 1, wherein the method does not comprise amplifying the target polynucleotides of the at least two samples using polymerase chain reaction.

14. The method of claim 1, wherein the sequence that binds to the adapter binding site is a flow cell binding sequence.

15. A method for normalizing the concentration of target polynucleotides between at least two samples each comprising target polynucleotides, the method comprising, for each sample of the at least two samples:
   (i) obtaining the sample, wherein the target polynucleotides of the sample comprise:
      a first adapter sequence comprising: a proximal portion, and a distal portion comprising a sequence that binds to an adapter binding site of a next-generation sequencing platform during next-generation sequencing; and
      a second adapter sequence;
   (ii) contacting the target polynucleotides with primers that are complementary to the proximal portion of the first adapter sequence;
   (iii) extending the primers to produce reverse complements of the target polynucleotides that do not comprise a reverse complement of the distal portion of the first adapter sequence, thereby producing partially double stranded polynucleotides comprising a double stranded second adapter sequence;
   (iv) producing a solution, the producing comprising combining: (a) the partially double stranded polynucleotides, (b) a predetermined concentration of a guide polynucleotide comprising a targeting region that is complementary to a strand of the double stranded second adapter sequence; and (c) a predetermined concentration of a dCas or a dArgonaute comprising an affinity tag; and
   (v) contacting the solution with a pre-determined amount of a catalytically active Cas or Argonaute protein to normalize the concentration of target polynucleotides between the two or more samples.

16. A method for normalizing the concentration of target polynucleotides between at least two samples each comprising target polynucleotides, the method comprising:
   (i) obtaining the at least two samples, wherein the target polynucleotides of the at least two samples comprise:
      a first adapter sequence comprising: a proximal portion, and a distal portion comprising a sequence that binds to an adapter binding site of a next-generation sequencing platform during next-generation sequencing; and
      a second adapter sequence;
   (ii) contacting each of the at least two samples with primers that are complementary to the proximal portion of the first adapter sequence;
   (iii) extending the primers in each of the at least two samples to produce reverse complements of the target polynucleotides that do not comprise a reverse complement of the distal portion of the first adapter sequence, thereby producing partially double stranded polynucleotides comprising a double stranded second adapter sequence;

(iv) binding the double stranded polynucleotides of each of the at least two samples with a predetermined amount of a ribonucleotide protein (RNP) complex, the RNP complex comprising: a dCas or a dArgonaute, and a guide polynucleotide that comprises a targeting region which is complementary to a strand of the double stranded second adapter sequence;

and (v) extracting the target polynucleotides from the RNP complex to normalize the concentration of target polynucleotides between the at least two samples.

17. The method of claim 16, wherein the RNP complex comprises a dCas protein and a Cas guide RNA.

18. The method of claim 17, wherein the Cas guide RNA comprises a homology region of any one of SEQ ID NOs: 1-26, and the dCas protein is dCas9.

19. The method of claim 18, wherein the Cas gRNA polynucleotide comprises a homology region of SEQ ID NO: 1.

20. The method of claim 16, wherein extracting the target polynucleotides from the RNP complex comprising contacting the RNP with a solid phase comprising an RNP complex binding molecule.

21. The method of claim 20, wherein extracting the target polynucleotides from the RNP complex comprises washing the solid phase.

22. The method of claim 16, wherein the method does not comprise amplifying the target polynucleotides of the at least two samples using polymerase chain reaction.

23. The method of claim 16, wherein obtaining the at least two samples comprises:
(i) obtaining at least fifty samples, wherein the target polynucleotides of the at least fifty samples comprise:
a first adapter sequence comprising: a proximal portion, and a distal portion comprising a sequence that binds to an adapter binding site of a next-generation sequencing platform during next-generation sequencing; and
a second adapter sequence;
(ii) contacting each of the at least fifty samples with primers that are complementary to the proximal portion of the first adapter sequence;
iii) extending the primers in each of the at least fifty samples to produce reverse complements of the target polynucleotides that do not comprise a reverse complement of the distal portion of the first adapter sequence, thereby producing partially double stranded polynucleotides comprising a double stranded second adapter sequence;
(iv) binding the double stranded polynucleotides of each of the at least fifty samples with a predetermined amount of a ribonucleotide protein (RNP) complex, the RNP complex comprising: a dCas9, a guide RNA that comprises a homology which is complementary to a strand of the double stranded second adapter sequence, and an affinity tag; and
(v) extracting the target polynucleotides from the RNP complex to normalize the concentration of target polynucleotides between the at least fifty samples, the extracting comprising contacting the RNP with a solid phase comprising an affinity tag binding molecule and washing the solid phase.

24. The method of claim 16, wherein the sequence that binds to the adapter binding site is a flow cell binding sequence.

25. The method of 20, wherein the RNP comprises an affinity tag and the RNP complex binding molecule comprises an affinity tag binding molecule.

* * * * *

```
                              SEQUENCE LISTING

Sequence total quantity: 50
SEQ ID NO: 1            moltype = RNA  length = 20
FEATURE                 Location/Qualifiers
source                  1..20
                        mol_type = other RNA
                        organism = synthetic construct
SEQUENCE: 1
gatcggaaga gcgtcgtgta                                                    20

SEQ ID NO: 2            moltype = RNA  length = 20
FEATURE                 Location/Qualifiers
source                  1..20
                        mol_type = other RNA
                        organism = synthetic construct
SEQUENCE: 2
agatcggaag agcgtcgtgt                                                    20

SEQ ID NO: 3            moltype = RNA  length = 20
FEATURE                 Location/Qualifiers
source                  1..20
                        mol_type = other RNA
                        organism = synthetic construct
SEQUENCE: 3
agcgtcgtgt agggaaagag                                                    20

SEQ ID NO: 4            moltype = RNA  length = 20
FEATURE                 Location/Qualifiers
source                  1..20
                        mol_type = other RNA
                        organism = synthetic construct
SEQUENCE: 4
agagcgtcgt gtagggaaag                                                    20

SEQ ID NO: 5            moltype = RNA  length = 20
FEATURE                 Location/Qualifiers
source                  1..20
                        mol_type = other RNA
                        organism = synthetic construct
SEQUENCE: 5
gaagagcgtc gtgtagggaa                                                    20

SEQ ID NO: 6            moltype = RNA  length = 20
FEATURE                 Location/Qualifiers
source                  1..20
                        mol_type = other RNA
                        organism = synthetic construct
SEQUENCE: 6
atcggaagag cgtcgtgtag                                                    20

SEQ ID NO: 7            moltype =    length =
SEQUENCE: 7
000

SEQ ID NO: 8            moltype =    length =
SEQUENCE: 8
000

SEQ ID NO: 9            moltype = RNA  length = 20
FEATURE                 Location/Qualifiers
source                  1..20
                        mol_type = other RNA
                        organism = synthetic construct
SEQUENCE: 9
agttcagacg tgtgctcttc                                                    20

SEQ ID NO: 10           moltype = RNA  length = 20
FEATURE                 Location/Qualifiers
source                  1..20
```

```
                            mol_type = other RNA
                            organism = synthetic construct
SEQUENCE: 10
gtgactggag ttcagacgtg                                                        20

SEQ ID NO: 11               moltype = RNA   length = 20
FEATURE                     Location/Qualifiers
source                      1..20
                            mol_type = other RNA
                            organism = synthetic construct
SEQUENCE: 11
cacatctgag acgctgccga                                                        20

SEQ ID NO: 12               moltype = RNA   length = 20
FEATURE                     Location/Qualifiers
source                      1..20
                            mol_type = other RNA
                            organism = synthetic construct
SEQUENCE: 12
atacacatct gagacgctgc                                                        20

SEQ ID NO: 13               moltype = RNA   length = 20
FEATURE                     Location/Qualifiers
source                      1..20
                            mol_type = other RNA
                            organism = synthetic construct
SEQUENCE: 13
ggctcggaga tgtgtataag                                                        20

SEQ ID NO: 14               moltype = RNA   length = 20
FEATURE                     Location/Qualifiers
source                      1..20
                            mol_type = other RNA
                            organism = synthetic construct
SEQUENCE: 14
tgggctcgga gatgtgtata                                                        20

SEQ ID NO: 15               moltype = RNA   length = 20
FEATURE                     Location/Qualifiers
source                      1..20
                            mol_type = other RNA
                            organism = synthetic construct
SEQUENCE: 15
gggctcggag atgtgtataa                                                        20

SEQ ID NO: 16               moltype = RNA   length = 20
FEATURE                     Location/Qualifiers
source                      1..20
                            mol_type = other RNA
                            organism = synthetic construct
SEQUENCE: 16
gtgggctcgg agatgtgtat                                                        20

SEQ ID NO: 17               moltype = RNA   length = 20
FEATURE                     Location/Qualifiers
source                      1..20
                            mol_type = other RNA
                            organism = synthetic construct
SEQUENCE: 17
ggagacacgc agggatgaga                                                        20

SEQ ID NO: 18               moltype = RNA   length = 20
FEATURE                     Location/Qualifiers
source                      1..20
                            mol_type = other RNA
                            organism = synthetic construct
SEQUENCE: 18
agtcggagac acgcagggat                                                        20

SEQ ID NO: 19               moltype = RNA   length = 20
FEATURE                     Location/Qualifiers
source                      1..20
                            mol_type = other RNA
                            organism = synthetic construct
SEQUENCE: 19
gagacacgca gggatgagat                                                        20

SEQ ID NO: 20               moltype =     length =
SEQUENCE: 20
```

```
000

SEQ ID NO: 21            moltype = RNA   length = 20
FEATURE                  Location/Qualifiers
source                   1..20
                         mol_type = other RNA
                         organism = synthetic construct
SEQUENCE: 21
gtcggagaca cgcagggatg                                                    20

SEQ ID NO: 22            moltype = RNA   length = 20
FEATURE                  Location/Qualifiers
source                   1..20
                         mol_type = other RNA
                         organism = synthetic construct
SEQUENCE: 22
gagtcggaga cacgcaggga                                                    20

SEQ ID NO: 23            moltype = RNA   length = 20
FEATURE                  Location/Qualifiers
source                   1..20
                         mol_type = other RNA
                         organism = synthetic construct
SEQUENCE: 23
actgcccata gagaggaaag                                                    20

SEQ ID NO: 24            moltype = RNA   length = 20
FEATURE                  Location/Qualifiers
source                   1..20
                         mol_type = other RNA
                         organism = synthetic construct
SEQUENCE: 24
atcaccgact gcccatagag                                                    20

SEQ ID NO: 25            moltype = RNA   length = 20
FEATURE                  Location/Qualifiers
source                   1..20
                         mol_type = other RNA
                         organism = synthetic construct
SEQUENCE: 25
gcccatagag aggaaagcgg                                                    20

SEQ ID NO: 26            moltype = RNA   length = 20
FEATURE                  Location/Qualifiers
source                   1..20
                         mol_type = other RNA
                         organism = synthetic construct
SEQUENCE: 26
gcctccgctt tcctctctat                                                    20

SEQ ID NO: 27            moltype = DNA   length = 29
FEATURE                  Location/Qualifiers
source                   1..29
                         mol_type = other DNA
                         organism = synthetic construct
SEQUENCE: 27
aatgatacgg cgaccaccga gatctacac                                          29

SEQ ID NO: 28            moltype = DNA   length = 33
FEATURE                  Location/Qualifiers
source                   1..33
                         mol_type = other DNA
                         organism = synthetic construct
SEQUENCE: 28
acactctttc cctacacgac gctcttccga tct                                     33

SEQ ID NO: 29            moltype = DNA   length = 24
FEATURE                  Location/Qualifiers
source                   1..24
                         mol_type = other DNA
                         organism = synthetic construct
SEQUENCE: 29
atctcgtatg ccgtcttctg cttg                                               24

SEQ ID NO: 30            moltype = DNA   length = 34
FEATURE                  Location/Qualifiers
source                   1..34
                         mol_type = other DNA
                         organism = synthetic construct
```

```
SEQUENCE: 30
agatcggaag agcacacgtc tgaactccag tcac                                34

SEQ ID NO: 31           moltype = DNA   length = 29
FEATURE                 Location/Qualifiers
source                  1..29
                        mol_type = other DNA
                        organism = synthetic construct
SEQUENCE: 31
aatgatacgg cgaccaccga gatctacac                                      29

SEQ ID NO: 32           moltype = DNA   length = 35
FEATURE                 Location/Qualifiers
source                  1..35
                        mol_type = other DNA
                        organism = synthetic construct
SEQUENCE: 32
tcgtcggcag cgtctcagat gtgtataaga gacag                               35

SEQ ID NO: 33           moltype = DNA   length = 24
FEATURE                 Location/Qualifiers
source                  1..24
                        mol_type = other DNA
                        organism = synthetic construct
SEQUENCE: 33
atctcgtatg ccgtcttctg cttg                                           24

SEQ ID NO: 34           moltype = DNA   length = 34
FEATURE                 Location/Qualifiers
source                  1..34
                        mol_type = other DNA
                        organism = synthetic construct
SEQUENCE: 34
ctgtctctta tacacatctc cgagcccacg agac                                34

SEQ ID NO: 35           moltype = DNA   length = 30
FEATURE                 Location/Qualifiers
source                  1..30
                        mol_type = other DNA
                        organism = synthetic construct
SEQUENCE: 35
ccatctcatc cctgcgtgtc tccgactcag                                     30

SEQ ID NO: 36           moltype = DNA   length = 41
FEATURE                 Location/Qualifiers
source                  1..41
                        mol_type = other DNA
                        organism = synthetic construct
SEQUENCE: 36
atcaccgact gcccatagag aggaaagcgg aggcgtagtg g                        41

SEQ ID NO: 37           moltype = AA    length = 1368
FEATURE                 Location/Qualifiers
source                  1..1368
                        mol_type = protein
                        organism = synthetic construct
SEQUENCE: 37
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDA    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK    1020
MIAKSEQEIG KATAKYFFYS NIMNFFKTEI TLANGEIRKR PLIETNGETG EIVWDKGRDF    1080
ATVRKVLSMP QVNIVKKTEV QTGGFSKESI LPKRNSDKLI ARKKDWDPKK YGGFDSPTVA    1140
YSVLVVAKVE KGKSKKLKSV KELLGITIME RSSFEKNPID FLEAKGYKEV KKDLIIKLPK    1200
YSLFELENGR KRMLASAGEL QKGNELALPS KYVNFLYLAS HYEKLKGSPE DNEQKQLFVE    1260
QHKHYLDEII EQISEFSKRV ILADANLDKV LSAYNKHRDK PIREQAENII HLFTLTNLGA    1320
```

```
PAAFKYFDTT IDRKRYTSTK EVLDATLIHQ SITGLYETRI DLSQLGGD              1368

SEQ ID NO: 38           moltype = AA  length = 1371
FEATURE                 Location/Qualifiers
source                  1..1371
                        mol_type = protein
                        organism = synthetic construct
SEQUENCE: 38
MDKKYSIGLD IGTNSVGWAV ITDDYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLADSTDKAD LRLIYLALAH MIKFRGHFLI EGDLNPDNSD  180
VDKLFIQLVQ TYNQLFEENP INASRVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAT  300
LLSDILRVNS EITKAPLSAS MIKRYDEHHQ DLTLLKALVR QQLPEKYKEI FFDQSKNGYA  360
GYIDGGASQE EFYKFIKPIL EKMDGTEELL AKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKAIVD LLFKTNRKVT VKQLKEDYFK KIECFDSVEI SGVEDRFNAS LGTYHDLLKI   600
IKDKDFLDNE ENEDILEDIV LTLTLFEDKE MIEERLKTYA HLFDDKVMKQ LKRRHYTGWG  660
RLSRKLINGI RDKQSGKTIL DFLKSDGFAN RNFIQLIHDD SLTFKEAIQK AQVSGQGHSL  720
HEQIANLAGS PAIKKGILQS VKVVDELVKV MGHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFIKDDS IDNKVLTRSD KNRGKSDDVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKRFFYSN IMNFFKTEIT LANGEIRKRP LIETNEETGE IVWDKGRDFA 1080
TVRKVLSMPQ VNIVKKTEVQ TGALTNESIY ARGSFDKLIS RKHRFESSKY GGFGSPTVTY 1140
SVLVVAKSKV QDGKVKKIKT GKELIGITLL DKLVFEKNPL KFIEDKGYGN VQIDCIKLP  1200
KYSLFEFENG TRRMLASVMA NNNSRGDLQK ANEMFLPAKL VTLLYHAHKI ESSKELEHEA 1260
YILDHYNDLY QLLSYIERFA SLYVDVEKNI SKVKELFSNI ESYSISEICS SVINLLTLTA 1320
SGAPADFKFL GTTIPRKRYG SPQSILSSTL IHQSITGLYE TRIDLSQLGS D          1371

SEQ ID NO: 39           moltype = AA  length = 748
FEATURE                 Location/Qualifiers
source                  1..748
                        mol_type = protein
                        organism = synthetic construct
SEQUENCE: 39
MNNLTFEAFE GIGQLNELNF YKYRLIGKGQ IDNVHQAIWS VKYKLQANNF FKPVFVKGEI   60
LYSLDELKVI PEFENVEVIL DGNIILSISE NTDIYKDVIV FYINNALKNI KDITNYRKYI  120
TKNTDEIICK SILTTNLKYQ YMKSEKGFKL QRKFKISPVV FRNGKVILYL NCSSDFSTDK  180
SIYEMLNNGL DVVGLQVKNR WTNSNGNIFI EEVLDKSISE PGTSGKLGQS LIDYYINGNQ  240
KYRVEKFTDE DKKAKVIKAK IKNKTYNYIP QALTPVITRE YLSHTDKKFS KQIENVIKMD  300
MNYRYQTLKS FVEDIGVIKE LNNLHFKNQY YTNFDFMGFE SGILEEPVLM GANGKIKDKK  360
QIFINGFFKN PKENVKFGVL YPEGCMENAQ SIARSILDFA TAGKYNKQEN KYISKNLMNI  420
GFKPSECIFE SYKLGDITEY KATARKLKEH EKVGFVIAVI PDMNESEVEN PYNPFKKVWA  480
KLNIPSQMIT LKTTEKFKNI VDKSGLYYLH NIALNILGKI GGIPWIIKDM PGNIDCFIGL  540
DVGTREKGIH FPACSVLFDK YGKLINYYKP TIPQSGEKIA ETILQEIFDN VLISYKEENG  600
EYPKNIVIHR DGFSRENIDW YKEYFDKKGI KFNIIEVKKN IPVKIAKVVG SNICNPIKGS  660
YVLKNDKAFI VTTDIKDGVA SPNPLKIEKT YGDVEMKSIL EQIYSLSQIH VGSTKSLRLP  720
ITTGYADKIC KAIEYIPQGV VDNRLFFL                                    748

SEQ ID NO: 40           moltype = AA  length = 745
FEATURE                 Location/Qualifiers
source                  1..745
                        mol_type = protein
                        organism = synthetic construct
SEQUENCE: 40
MSNLTVEAFE GIGSVNPMLF YQYKVTGKGK YDNVYKIIKS ARYKMHSKNR FKPVFIKDDK   60
LYTLEKLPDI EDLDFANINF VKSEVLSIED NMSIYGEVVE YYINLKLKKV KVLGKYPKYR  120
INYSKEILSN TLLTRELKDE FKKSNKGFNL KRKFRISPVV NKMGKVILYL SCSADFSTNK  180
NIYEMLKEGL EVEGLAVKSE WSNISGNLVI ESVLETKISE PTSLGQSLID YYKNNQGYR   240
VKDFTDEDLN ANIVNVRGNK KIYMYIPHAL KPIITREYLA KNDPEFSKEI EQLIKMNMNY  300
RYETLKSFVN DIGVIEELNN LSFKNKYYED VKLLGYSSGK IDEPVLMGAK GIIKNKMQIF  360
SNGFYKLPEG KVRFGVLYPK EFDGVSRKAI RAIYDFSKEG KYHGESNKYI AEHLINVEFN  420
PKECIFEGYE LGDITEYKKA ALKLNNYNNV DFVIAIVPNM SDEEIENSYN PFKKIWAELN  480
LPSQMISVKT AEIFANSRDN TALYYLHNIV LGILGKIGGI PWVVKDMKGD VDCFVGLDVG  540
TREKGIHYPA CSVVFDKYGK LINYYKPNIP QNGEKINTEI LQEIFDKVLI SYEEENGAYP  600
KNIVIHRDGF SREDLDWYEN YFGKKNIKFN IIEVKKSTPL KIASINEGNI TNPEKGSYIL  660
RGNKAYMVTT DIKENLGSPK PLKIEKSYGD IDMLTALSQI YALTQIHVGA TKSLRLPITT  720
GYADKICKAI EFIPQGRVDN RLFFL                                       745

SEQ ID NO: 41           moltype = AA  length = 771
FEATURE                 Location/Qualifiers
source                  1..771
                        mol_type = protein
                        organism = synthetic construct
SEQUENCE: 41
SMKAIVVINL VKINKKIIPD KIYVYRLFND PEEELQKEGY SIYRLAYENV GIVIDPENLI   60
```

```
IATTKELEYE GEFIPEGEIS FSELRNDYQS KLVLRLLKEN GIGEYELSKL LRKFRKPKTF   120
GDYKVIPSVE MSVIKHDEDF YLVIHIIHQI QSMKTLWELV NKDPKELEEF LMTHKENLML   180
KDIASPLKTV YKPCFEEYTK KPKLDHNQEI VKYWYNYHIE RYWNTPEAKL EFYRKFGQVD   240
LKQPAILAKF ASKIKKNKNY KIYLLPQLVV PTYNAEQLES DVAKEILEYT KLMPEERKEL   300
LENILAEVDS DIIDKSLSEI EVEKIAQELE NKIRVRDDKG NSVPISQLNV QKSQLLLWTN   360
YSRKYPVILP YEVPEKFRKI REIPMFIILD SGLLADIQNF ATNEFRELVK SMYYSLAKKY   420
NSLAKKARST NEIGLPFLDF RGKEKVITED LNSDKGIIEV VEQVSSFMKG KELGLAFIAA   480
RNKLSSEKFE EIKRRLFNLN VISQVVNEDT LKNKRDKYDR NRLDLFVRHN LLFQVLSKLG   540
VKYYVLDYRF NYDYIIGIDV APMKRSEGYI GGSAVMFDSQ GYIRKIVPIK IGEQRGESVD   600
MNEFFKEMVD KFKEFNIKLD NKKILLLRDG RITNNEEEGL KYISEMFDIE VVTMDVIKNH   660
PVRAFANMKM YFNLGGAIYL IPHKLKQAKG TPIPIKLAKK RIIKNGKVEK QSITRQDVLD   720
IFILTRLNYG SISADMRLPA PVHYAHKFAN AIRNEWKIKE EFLAEGFLYF V            771

SEQ ID NO: 42            moltype = AA  length = 706
FEATURE                  Location/Qualifiers
source                   1..706
                         mol_type = protein
                         organism = synthetic construct
SEQUENCE: 42
MKNLRYKINA YRIKKDYIPK EVYRYRIRSF IENINIYRFV GFYGGVALNQ SEFILPYPVE    60
NLVLEYDGKD VKLEHIDTLN LEDIENKDKE KAEKLVRGYL TSIYKLKPIL YKILRDVRES   120
KIINDIRVDP IPDFTVKRHN NEYYLVIDFN HTATVLKNLW DFVGRDKLKL EDYIGKKIIF   180
KPNPKKRYTI KSIEKQNKKD IDDIVEHIIE YYKWTEEEIK STFGEIDYTQ PIIHCEGIPY   240
PPFAPQFCNIV FTMEDLDENT LKDLQSYWRL PNEIKGNIIN QIAKKLRFVE NEPIELEFIK   300
FNNTPLIVKD ENGKPTKIYT TNRLFRWNYD SKSKLYLPYD IPDIIKNKTL TTFVLIDENL   360
KNVSGKIKRK VYQMFKNYNK IASKTELPKF DFANKWKYFS NNNIRDVIRK IKDEFNEELG   420
FALIIGNRYY ENDYYETLKM QLFNLNIISQ NILWENWSKD DNNFMTNNLL IQIMGKLGIK   480
YFALDAKVNY DYIMGLDSGL GAFKSNRVSG CTVIYDSEGK IRRIQPIDVP SPGERIPIHL   540
VVEFLETKTD INMENKNILF LRDGFVQNSE REELKKLSKE LNSNIEVISI RKNNKYKVFT   600
SDYGIGSIFG NDGIFLPHKT TFGSNPVKLS TWLRFNSGNE EKLKINESIM QLLYDLTKMN   660
YSALYGEGRN LRIPAPIHYA DKFVKALGKN WKIDEELLKH GFLYFI                  706

SEQ ID NO: 43            moltype = AA  length = 402
FEATURE                  Location/Qualifiers
source                   1..402
                         mol_type = protein
                         organism = synthetic construct
SEQUENCE: 43
MLVNGFKLKI PLIAKDHENR VVEIYSTSTV LKEKFVPYEI PQFIRGREIE TWILIDKEIK    60
DNFQEIKKTV IEFFRYYNSI RNNLLPYFKF SYNYVIFSRQ NVFKVLTKMN GVDSDAVGFA   120
LIIGKQKYRN SDYYEEIKRI LFNKNIISQN VLWDQGTLKN NFARNNIIIQ ILSKLGIKYF   180
VLKYNAEYDY IFGVDIGKEK FSGSSLGGCT IIYDYKGELK KIVPIEILAK KETLNLERIF   240
ETLQLDMNLE GKKILLLRDG SIKNFEKEQL KNISKRYHVE ITTLNIKKYS KFRIGNDEGG   300
IGVLIEDIAL LLPHHYPYGS KPIKIDNKIL FKDGNYTELE INANDLELIY GLSKLNYSSL   360
SSEERILRLP APVHYAHKFV KALGKGWKIR KDLLEEGCLY FI                      402

SEQ ID NO: 44            moltype = AA  length = 782
FEATURE                  Location/Qualifiers
source                   1..782
                         mol_type = protein
                         organism = synthetic construct
SEQUENCE: 44
MMLNIFEVDK NRVEVPQDVY LYKVHLKTLE QRKRDMCIAV LRNSFGYLDV NSFVIYSYKE    60
IRDLPRRIKK YCDLEPTGKV KMNEVDENVR NALVKTFLRS KIRKDIKKLL KKFKKFQQSV   120
GRWTVALDLE RIELVEHNGE ILVSFNVKLN ISSMINLWDI IERDVNRLKG LCWSPENLND   180
NRIWFRYIPH LIIEEVEDFE ESAKSFILSD VHTGEEFGGW TTEDLKKYPE NEYGLSEDAI   240
KKIGNYTQFD STQPIIKGVT WSGKEYPFLP QHCIPAYNPM LATAEEKKRI EEIKINLKNK   300
KDEIIRKIIE QLPYLKQPDN IEIKKVQETA RLRAKFVKVE VTKGKITKTL SQPYEKPVSS   360
TLDLFGWISR IIDGGDGIIE ICIPDYIPEN LSRIKEIEAF LLIENDLNEN ERKVGDKLLN   420
DAIYVYNFVR SVCLRCGINI PYLNYKGNRF YFENSKEGIR DIYKRITTSL SGEIGFALIF   480
GKRDNYEDEE GEDSFDYYNP LKSALFRNNI LSQNFDVTNY VRGDGKINKN TIKYAVSNII   540
YNIFGKLGVK FFVLEEDVPY DYILGIDVGY GEAYTGKVAG CTTVHDSEGR LRNLIPIEKQ   600
NYPSKETARI KALLEEIEQK KKIYNIDFEN KSILILRDGN INKEEINQLM EFSEERNCRI   660
TYIEIRKNIV HQFLVNSSQA CYVKIGDYYI LKAHNPRIGF PRAIKIARKI VIEGGDAWRES  720
SLTEDDILLI YKLTALNYST IGRDSNLRIP APIYYADKLV KALKKGWKFD ERFLRYGILY   780
FL                                                                  782

SEQ ID NO: 45            moltype = AA  length = 817
FEATURE                  Location/Qualifiers
source                   1..817
                         mol_type = protein
                         organism = synthetic construct
SEQUENCE: 45
MKGRNNSSLK LNIFRVNLEQ LSIPEKIYVY NISANILDSS KLTSFYKRLE NIYGFMDTQN    60
RKLYSYKEID FISKNMKENL NLKLEKTIKL SELESSFRNQ ILKTYIRNSV KMDINRIIKE   120
IQHQFLGKEK KRTGRWNLSI IPERINVEHI NDAFYVAFNV KLRILANKNL WDFIGRDLEK   180
LKTLCWFPDK SKDIKIWFRY VPDLKEENER SYLLTYIQSK DEAKNSGFSF EDLKYYPQEK   240
RNTTYGELKE IAKFEDFDEN QPIIVGVSST DMRNPLYFLP QYCIPAYNPV LASENESKKI   300
QKVYESVLFR NKYEIIYKIY DKIPYLELNY EDISFKELDN HRKGKLKVNF VKAKLYLGKD   360
```

```
KKDKQGKEII KCKVVGKPQK RTIENTADLF SWIHKLEDLR GKKKKELIVD IPIPEYVPEY    420
LQKLDEIGTF LLVESGNPSS DIDMIKNFLL LIADVYRVIR EASEGFNKIP RLKFIKNPET    480
NRFEFLFKKS SEGIDKTVRE LGQLLKKGKK ELSEKELGFA FIFGSQDDFV EEHEDFDYYI    540
PLKRNLFLNN ILSQNFLIDT YTNKNKIKFA LSNIVYNLFG KLGIKFFALE EKVYYDYILG    600
IDTGLAEAYT GRVAGCTTVH DSNGRLKNII PIEKLNPARR ETVRIKALLE EIHIDADYNM    660
DFSNKKILIL RDGKIQPEEL KQLVEFTKSK KCKITMIDVR KHTVYQWLEK GNDKHLSIKV    720
GDFCLLKPHS PRRGYPRMLK ISQKVEIDEN GFTYKDLTDY DILLIYKLTL LNYSTIGRPS    780
NLKLPGPIYY ADKLVKALKR GWKLEPKFLK EGFLYFL                             817

SEQ ID NO: 46           moltype = RNA   length = 101
FEATURE                 Location/Qualifiers
source                  1..101
                        mol_type = other RNA
                        organism = synthetic construct
SEQUENCE: 46
gggcgaggag ctgttcaccg gtttttagagc tagaaatagc aagttaaaat aaggctagtc    60
cgttatcaac ttgaaaaagt ggcaccgagt cggtgctttt t                       101

SEQ ID NO: 47           moltype = AA    length = 6
FEATURE                 Location/Qualifiers
source                  1..6
                        mol_type = protein
                        organism = synthetic construct
SEQUENCE: 47
HHHHHH                                                                 6

SEQ ID NO: 48           moltype = RNA   length = 100
FEATURE                 Location/Qualifiers
source                  1..100
                        mol_type = other RNA
                        organism = synthetic construct
modified_base           1
                        mod_base = OTHER
                        note = 2prime-O-methyladenosine
modified_base           2
                        mod_base = OTHER
                        note = 2prime-O-methylguanosine
modified_base           3
                        mod_base = OTHER
                        note = 2prime-O-methyladenosine
modified_base           97..99
                        mod_base = OTHER
                        note = 2prime-O-methyluridine
modified_base           1..4
                        mod_base = OTHER
                        note = phosphorothioate linkages
modified_base           97..100
                        mod_base = OTHER
                        note = phosphorothioate linkages
SEQUENCE: 48
agatcggaag agcgtcgtgt gttttagagc tagaaatagc aagttaaaat aaggctagtc    60
cgttatcaac ttgaaaaagt ggcaccgagt cggtgctttt                         100

SEQ ID NO: 49           moltype = DNA   length = 21
FEATURE                 Location/Qualifiers
source                  1..21
                        mol_type = other DNA
                        organism = synthetic construct
SEQUENCE: 49
gtgactggag ttcagacgtg t                                               21

SEQ ID NO: 50           moltype = RNA   length = 36
FEATURE                 Location/Qualifiers
source                  1..36
                        mol_type = other RNA
                        organism = synthetic construct
SEQUENCE: 50
gcacggagac ggatgttatt gttttagagc tatgct                               36
```